United States Patent

Metz et al.

[11] Patent Number: 5,986,746
[45] Date of Patent: *Nov. 16, 1999

[54] TOPOGRAPHICAL OBJECT DETECTION SYSTEM

[75] Inventors: Michael Metz, Yorktown Heights, N.Y.; Nicholas J. Phillips, Loughborough, United Kingdom; Zane Coleman, Chicago, Ill.; Carl Flatow, Oceanside, N.Y.

[73] Assignee: Imedge Technology Inc., White plains, N.Y.

[*] Notice: This patent is subject to a terminal disclaimer.

[21] Appl. No.: 08/823,754

[22] Filed: Mar. 26, 1997

Related U.S. Application Data

[63] Continuation-in-part of application No. 08/394,470, Feb. 27, 1995, which is a continuation of application No. 08/198,998, Feb. 18, 1994, abandoned, and application No. 08/597,491, Feb. 2, 1996.

[51] Int. Cl.⁶ .................................................. G06K 9/24
[52] U.S. Cl. ................................................................ 356/71
[58] Field of Search ............................... 356/71; 382/124, 382/126, 127, 125

[56] References Cited

U.S. PATENT DOCUMENTS

| | | | |
|---|---|---|---|
| 4,728,186 | 3/1988 | Eguchi et al. | 356/71 |
| 5,448,659 | 9/1995 | Tsutsui et al. | 356/71 |
| 5,621,516 | 4/1997 | Shinzaki et al. | 356/71 |

*Primary Examiner*—Richard A. Rosenberger
*Attorney, Agent, or Firm*—Hopgood, Calimafde, Kalil & Judlowe, LLP

[57] ABSTRACT

A compact system for producing high contrast and high resolution images of a topographical surface associated with an object. The system utilizes a novel holographic optical element to produce images of topographical surfaces differentiating between ridges and valleys, and providing image details of artifacts. The system of the present invention can be realized in the form of a hand-held instrument for use in in vivo imaging of fingerprint, skin tissue and the like.

65 Claims, 13 Drawing Sheets

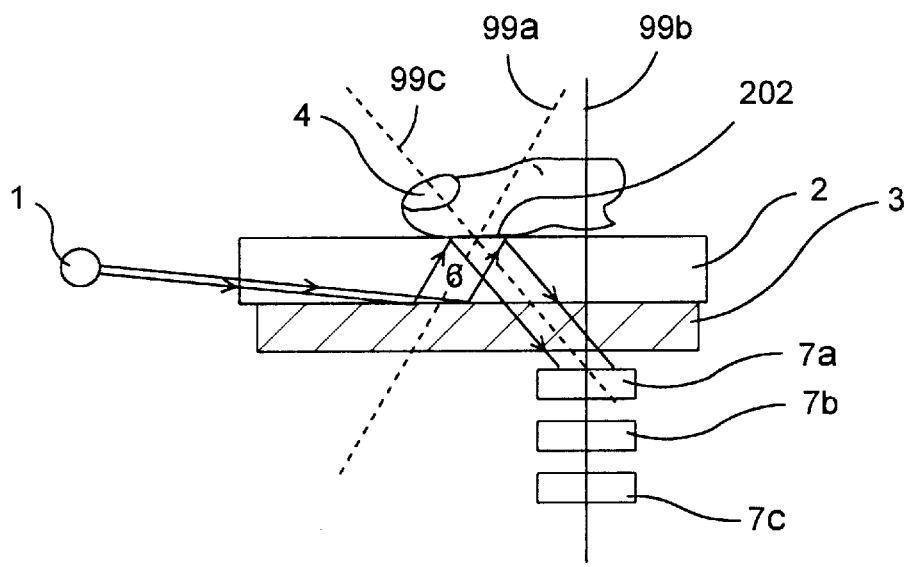
F I G. 3c
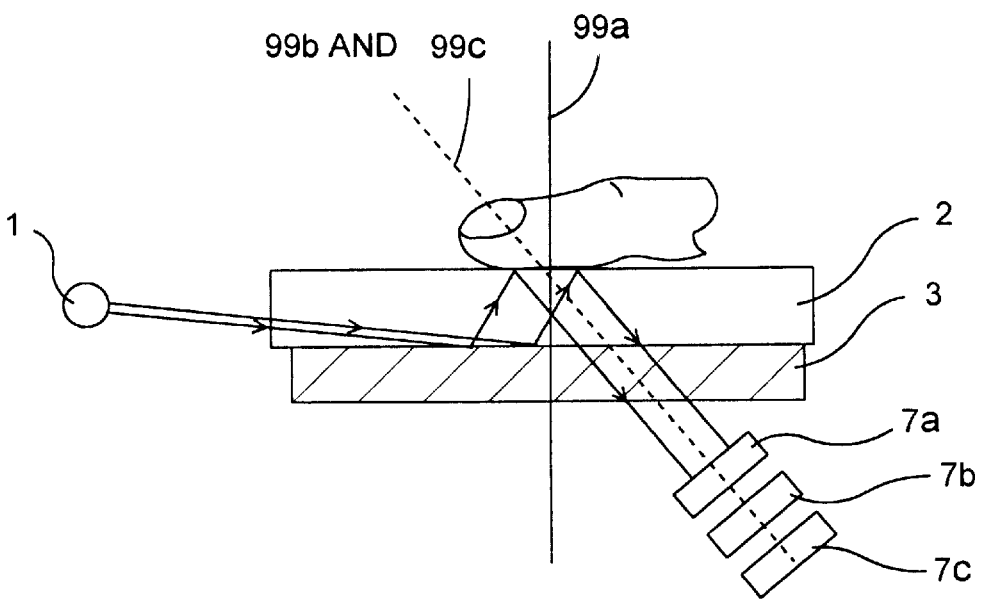
F I G. 3d

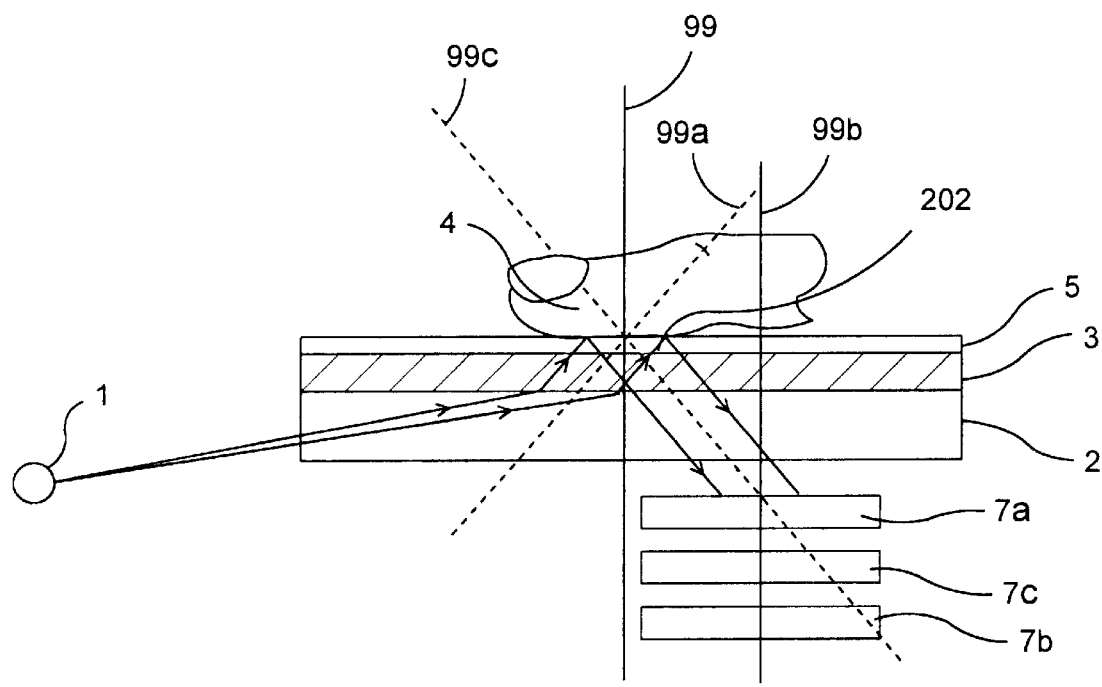
F I G. 3e
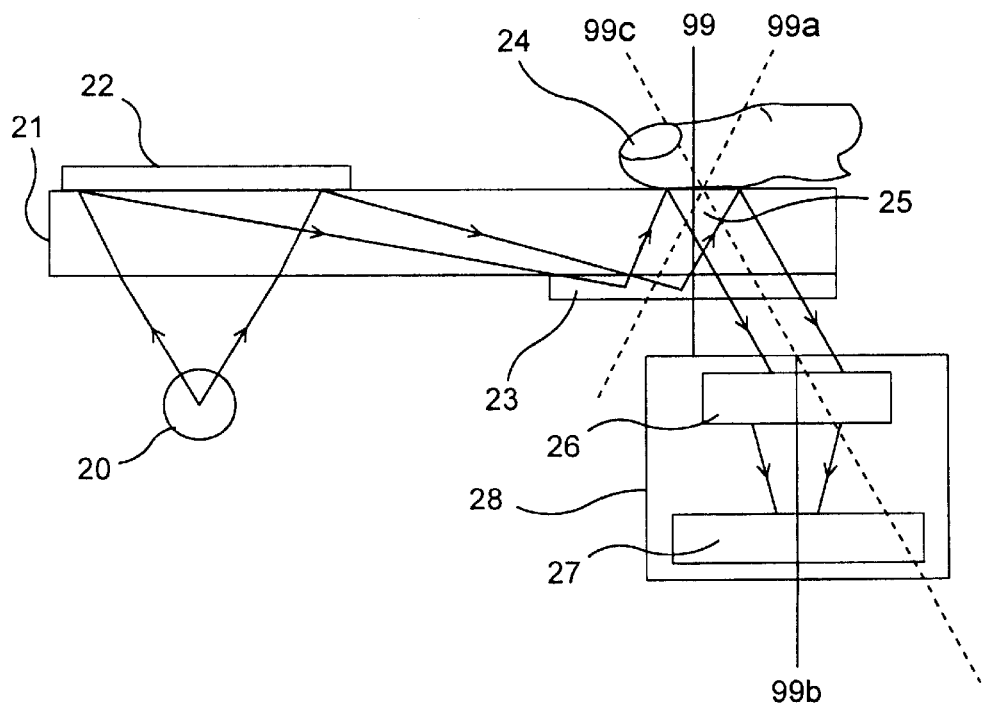
F I G. 4

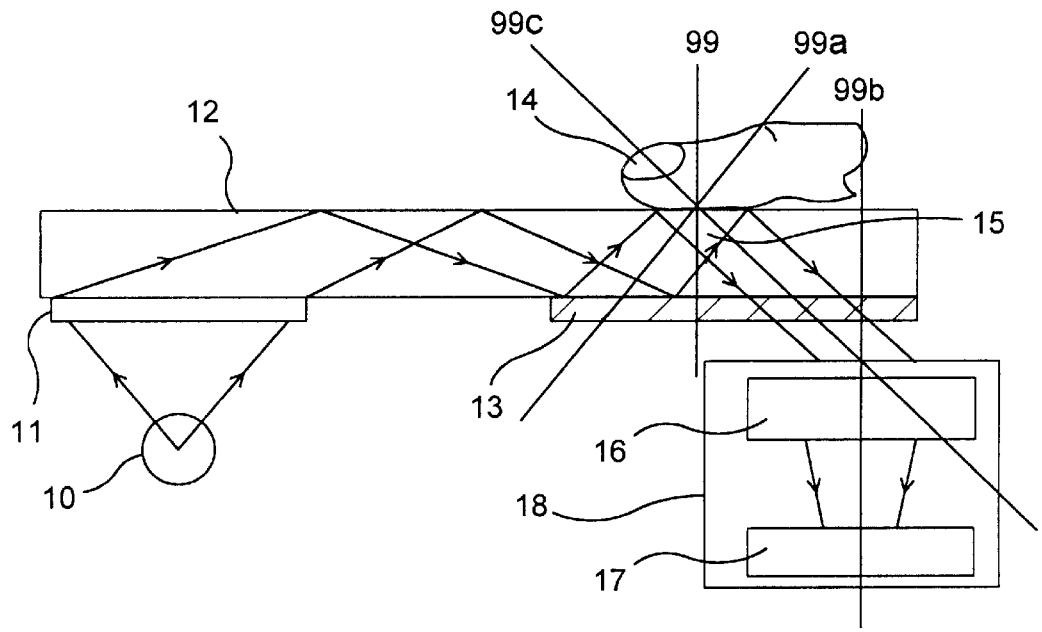
F I G. 5
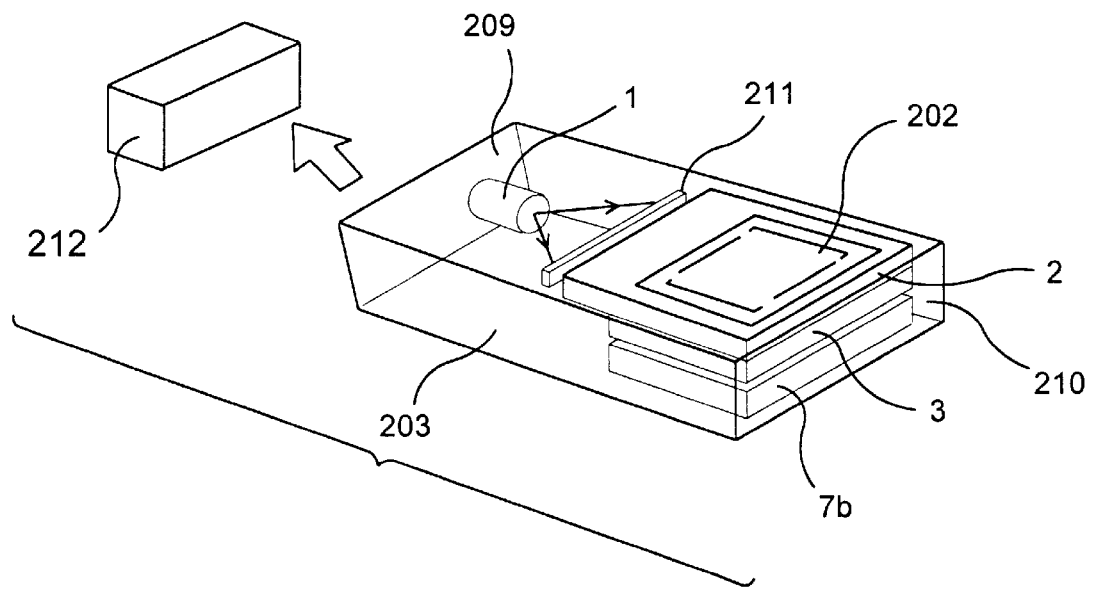
F I G. 6a

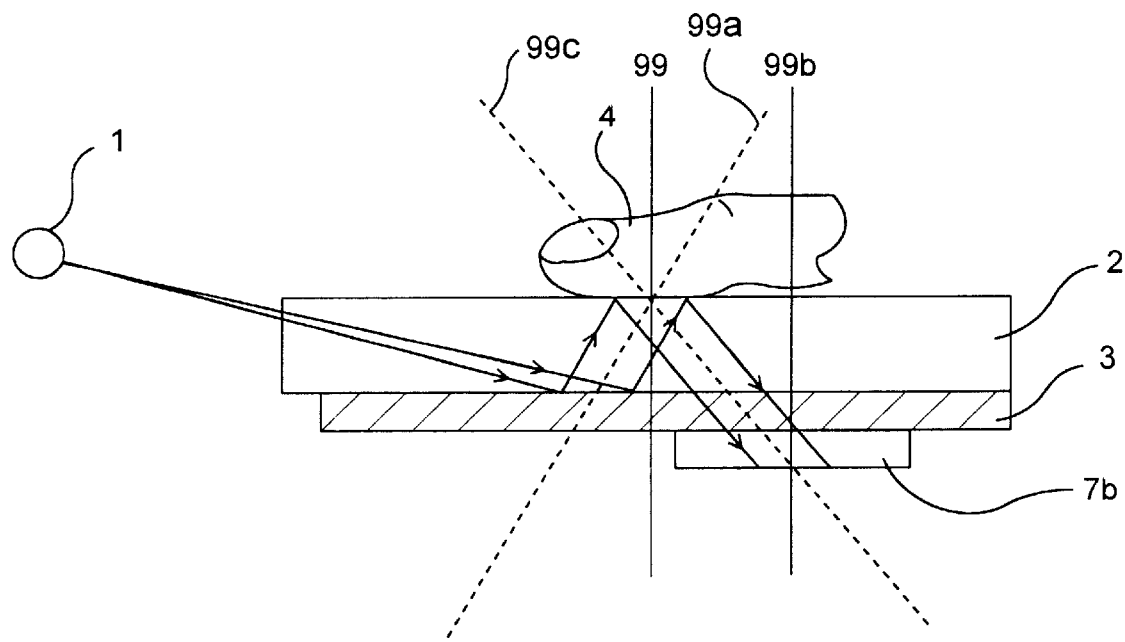
F I G. 6b
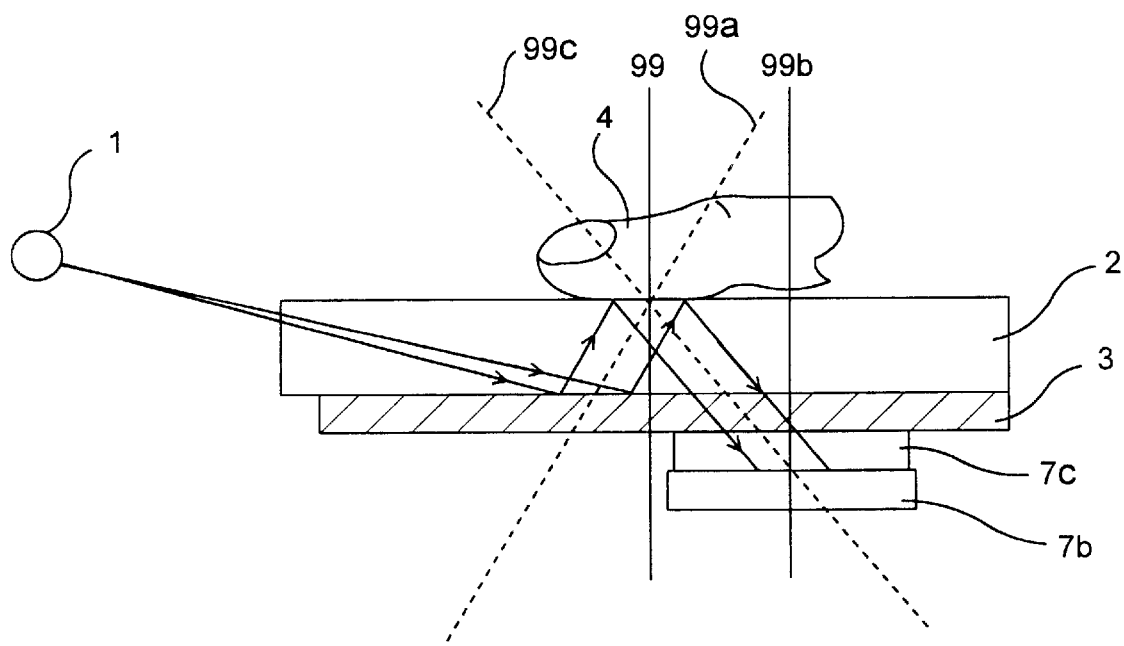
F I G. 6c

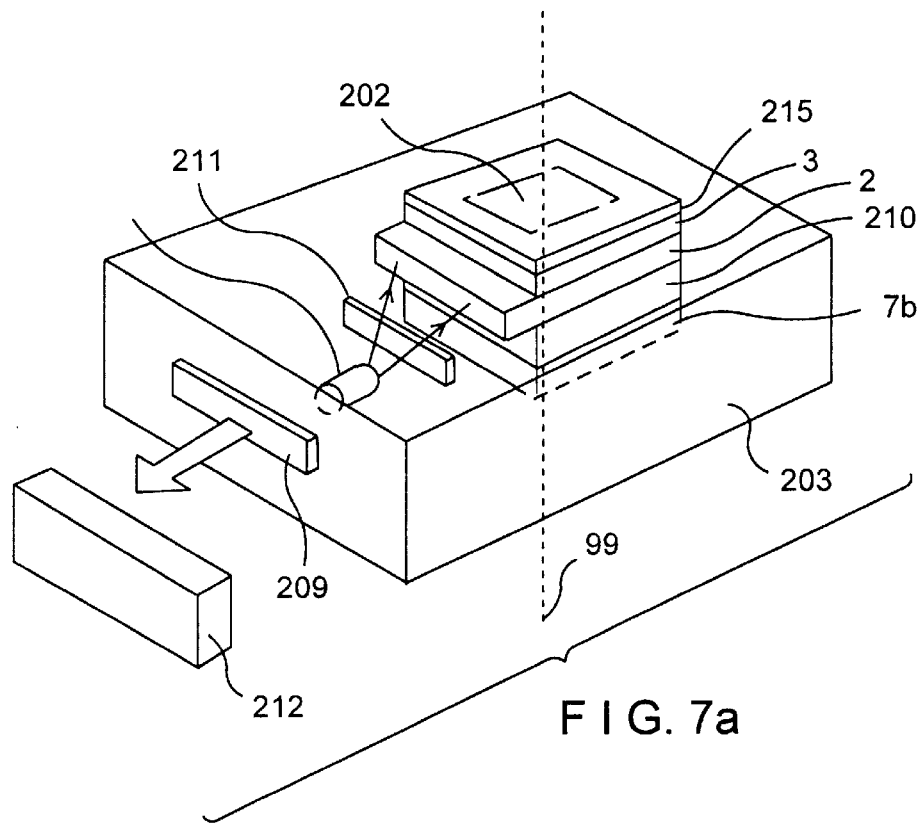
F I G. 7a
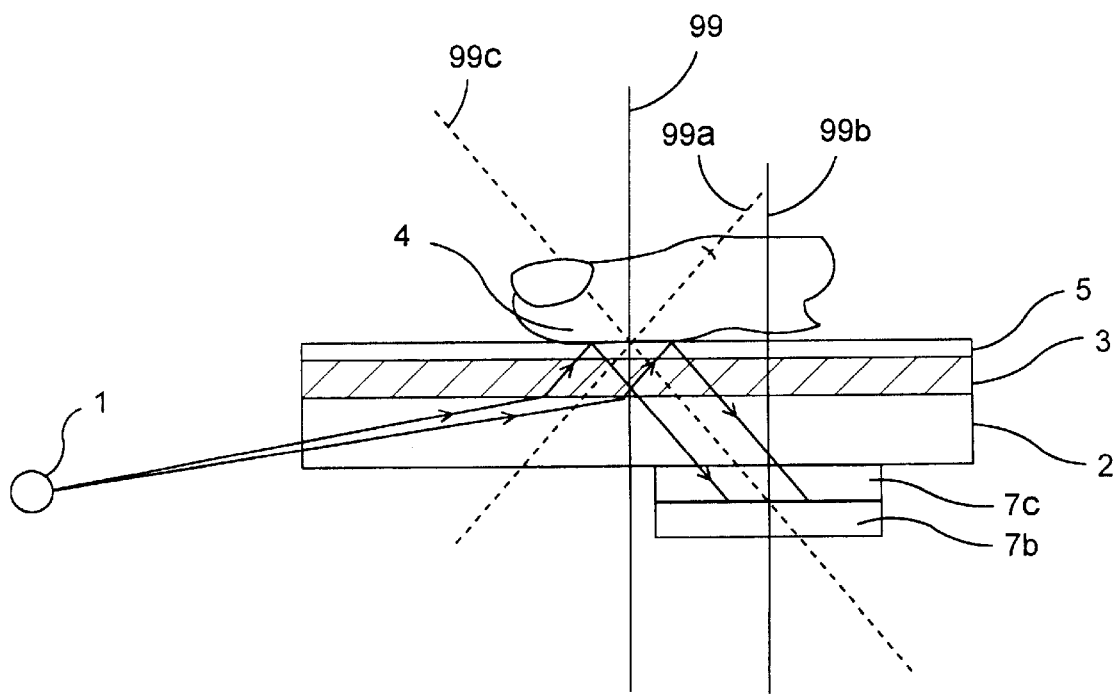
F I G. 7b

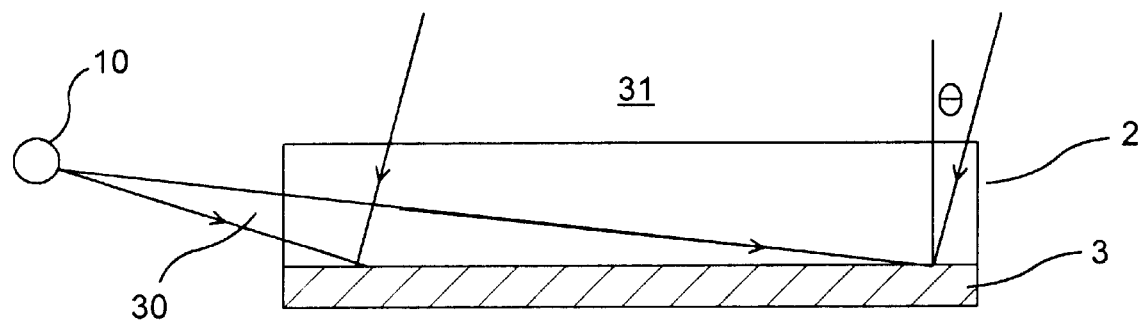
F I G. 11
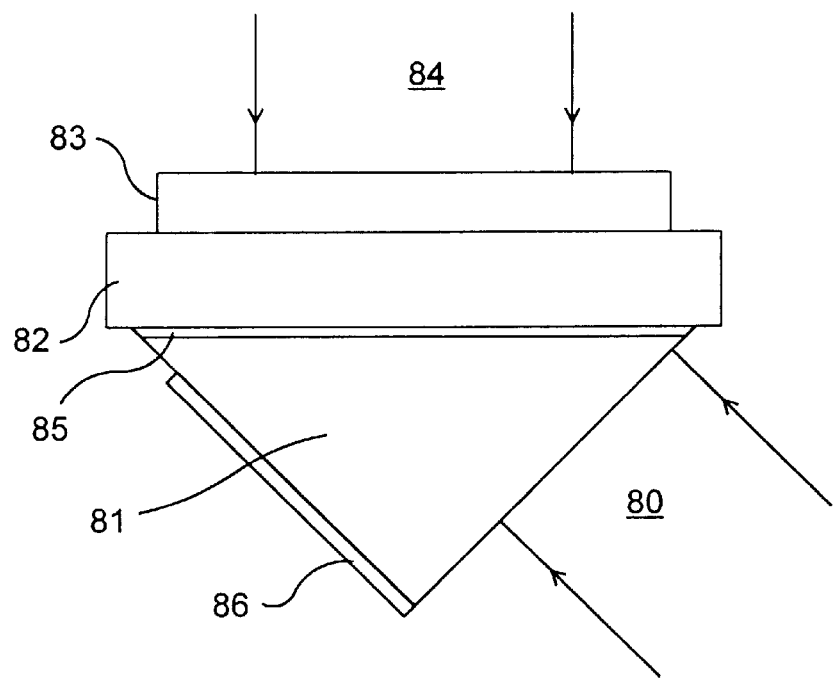
F I G. 12

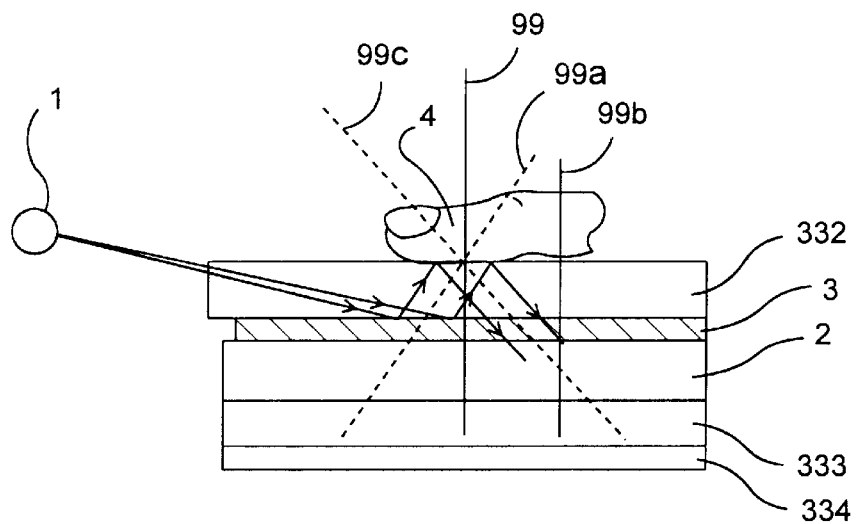
F I G. 15
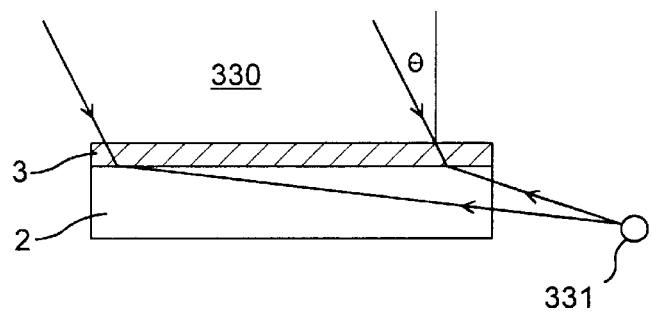
F I G. 15a
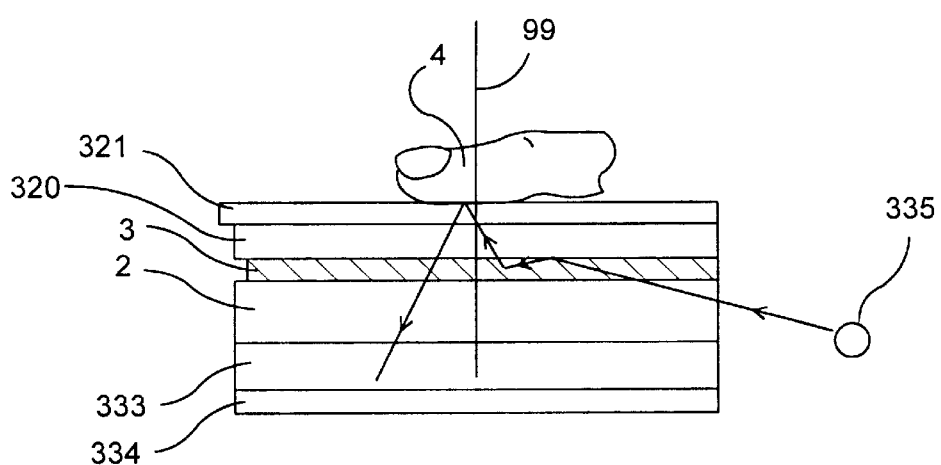
F I G. 16

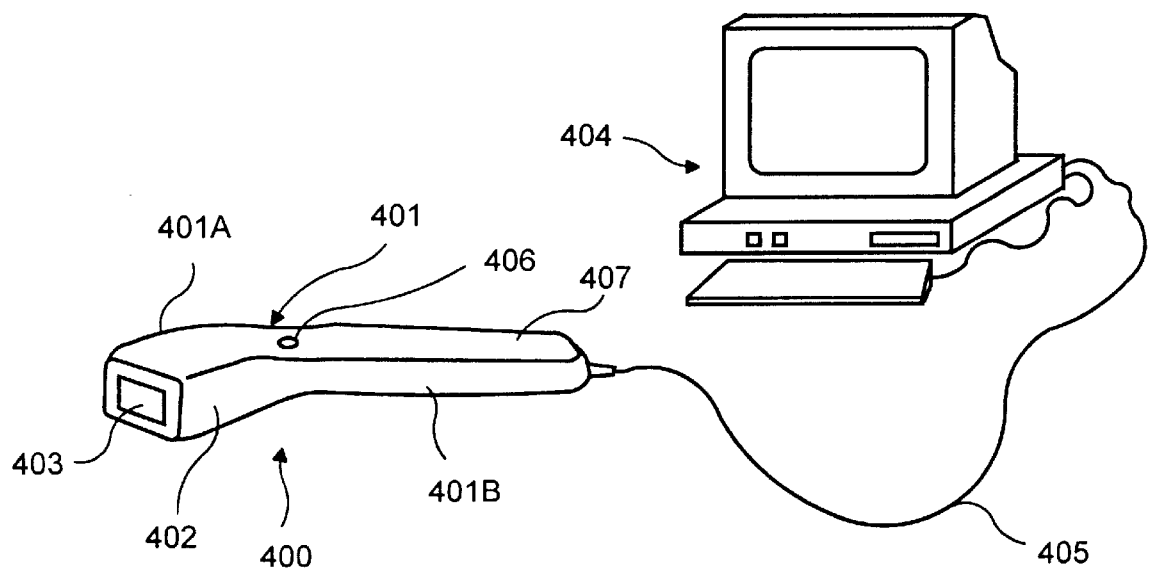
F I G. 17
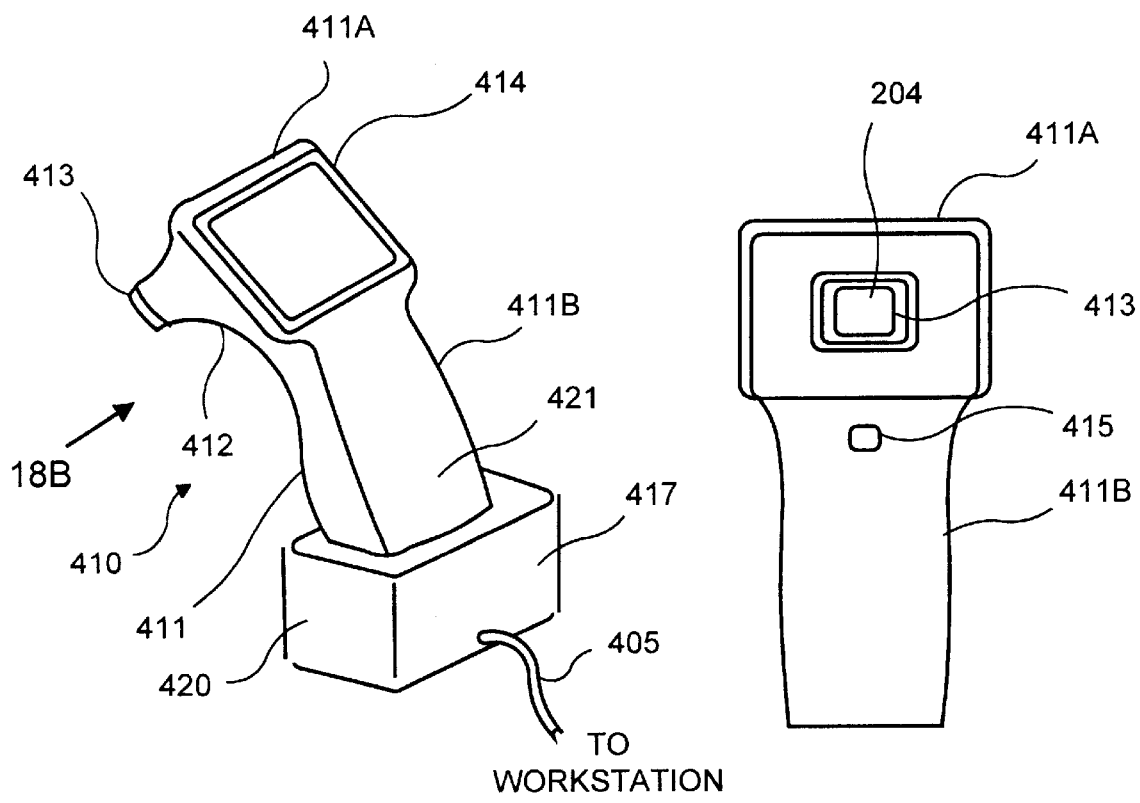
F I G. 18a
F I G. 18b

TOPOGRAPHICAL OBJECT DETECTION SYSTEM

RELATED CASES

This Application is a Continuation-in-Part of: Co-pending application Ser. No. 08/394,470, filed Feb. 27, 1995, which is a Continuation of application Ser. No. 08/198,998 entitled "Method of Producing and Detecting High-Contrast Images of The Surface Topography of Objects and a Compact System for Carrying Out the Same" filed by Michael H. Metz on Feb. 18, 1994, now abandoned; and copending application Ser. No. 08/597,491, entitled "Grazing Incidence Holograms and System and Method For Producing The Same" by Nicholas J. Phillips, filed Feb. 2, 1996; each of said Applications being commonly assigned to ImEdge Technology, Inc. of White Plains, N.Y. and incorporated herein by reference as if set forth in its entirety.

BACKGROUND OF THE INVENTION

1. Field of the Invention

The present invention relates to a method and apparatus for producing and detecting an image of a topographic surface such as a fingerprint, sample of skin tissue or the like for optical viewing, display, storage and/or processing.

2. Description of the Related Art

As technology advances and becomes more sophisticated, so too do criminals. Fraud costs our society billions of dollars worldwide each year. A growing industry has sprung up to develop new technologies and methods of preventing fraud. One important aspect of this is the need to positively identify an individual as the proper owner of a credit card, passport, or bank account, for example, or that the person is allowed access to a door, a computer, or other physically secured systems.

Numerous biometric devices are being developed to recognize human characteristics which can uniquely identify an individual. One of the oldest and best understood of the various biometric identifiers is fingerprints. Automated fingerprint capture systems connected to computer databases are replacing the long used inked fingerprints on paper. In addition to law enforcement applications, these automated fingerprint identification systems, known as 'live scan' devices, are being used in welfare, health care and motor vehicle offices, for employee time and attendance monitoring, and for secure keyless entry systems allowing access to computer networks, sensitive areas, offices, cars, homes, and hotel rooms.

Many methods have been proposed for optical detection of fingerprints and other topographic biometric features such as footprints and palmprints. Most of these methods utilize optical systems, typically incorporate a prism or beamsplitting apparatus, and operate on the principle of frustrated total internal reflection. Such systems are necessarily bulky, cannot detect certain skin detail information, such as valley or pore detail, or require expensive optical components. In addition some prior art systems suffer from distortion, poor signal to noise ratio, aberrations, lack of contrast, and/or lack of resolution of finger detail information. There are many patents which describe variations of optical systems wherein illuminating light is directed into a prism. The basic common concept as applied, for example, to inkless fingerprint detection, involves illuminating one side of a prism with light and pressing a finger onto another surface of the prism, usually the hypotenuse. A fingerprint image, formed by frustrated total internal reflection, is created where the finger meets the prism. Light passing out of the prism containing the fingerprint image is then captured by a detection system. For example, in U.S. Pat. No. 3,174,414, J. Myer describes an apparatus for recording fingerprints using photochemical or xerographic means separately or in combination with photographs. This U.S. patent shows various means of creating a fingerprint image by the principle of total internal reflection, using a prism, and other optical system parts to relay the fingerprint image. Many other such examples of prism based systems exist in the prior art, and can be found such as U.S. Pat. No. 3,482,498 to L. Becker and U.S. Pat. No. 3.947,128 to Z. Weinberger, et. al.

Other prior art systems illuminate and/or view the finger directly, without using the principle of total internal reflection. One such system is described in U.S. Pat. No. 3,138,059 to W. White. U.S. Pat. No. 5,177,802 to Y. Fujimoto, et. al. describes a system which uses a light guide plate having a through hole, so that the finger is in air, and light traveling through the light guide exits the light guide near the hole to illuminate the finger. The finger image is captured by a detection system directly opposite the finger. In another system, the finger rests on the light guide surface and operates by frustrated total internal reflection of the illuminating light traveling through the light guide. A third system is described which does not use a light guide, but uses linear light sources such as fluorescent tubes placed near the 'belly' of the finger to be imaged, and a detection system to image the finger directly. In embodiments, the finger is illuminated directly via light emerging from the light guide, the light strikes the finger at an angle, limiting uniformity of illumination and contrast. The embodiment utilizing fluorescent tube illumination additionally suffers from bulkiness and direct lamp light reaching the detector, reducing the signal to noise ratio of images produced using this system.

Other types of systems involving comparison and scanned illumination have been described. U.S. Pat. No. 3,511,571 describes a method wherein the surface of the finger is flooded with light. The light reflected from the finger may be passed through a transparency of a previously recorded fingerprint for direct comparison. U.S. Pat. No. 3,200,701 describes a system wherein light is scanned onto the finger and the reflected light produces an output which can yield a fingerprint image. U.S. Pat. Nos. 3,864,042 and 4,003,656 also describe systems for illuminating a finger with a scanning light beam.

Various methods have been proposed utilizing holograms as part of the fingerprint illumination and detection system. U.S. Pat. No. 5,109,427 describes a fingerprint recognition device which uses collimated laser light which illuminates the finger through a tetragonal prism. A hologram is used to shift the axis of the fingerprint image to a second optical axis. An objective lens then projects the fingerprint image to a CCD camera.

In the paper entitled "Real-time fingerprint sensor using a hologram", Applied Optics, Vol. 31, No. 11, p.1794ff, and in U.S. Pat. No. 4,728,186 entitled 'Uneven Surface Data Detection Apparatus', S. Eguchi, S. Igaki, et. al. describe a system wherein laser light illuminates a finger directly through, or via waveguiding through a substrate. The scattered light reflected from the finger travels through the substrate, which acts as a light pipe. A plain grating type hologram attached to the substrate allows rays with the proper angle to exit the substrate, wherein a lens then images the exiting light containing the fingerprint information to a CCD camera or other detector. Other embodiments include a hologram to direct the light to the finger, but the finger image still travels by total internal reflection to be output to a detection system located along a different optical axis from the finger. In the Eguchi system, a hologram is primarily used to extract the fingerprint information after the information has traveled through a waveguide. The input light path to the finger and the output light path to the detection system are necessarily along different optical axes. Expectedly, this prior art system suffers from loss of information due to imperfections in the waveguide or damage to the information in the form of additional noise, distortions or aberrations due to its travel through the waveguide and/or the hologram extracting means In addition, the geometry of this prior art system limits its ability to be extremely compact.

Other prior art systems use a hologram, but for different purposes. For example, in U.S. Pat. No. 4,053,228, a fingerprint is compared against a fingerprint which is stored on a hologram.

U.S. Pat. No. 3,430,300 to H. Ruell describes a means for forming a latent topographic relief of a finger pattern. It uses a deformable polymer which is illuminated through its edge and upon which a finger is pressed. The deformation caused by the finger causes frustrated total internal reflection which redirects the illuminating light at the points of frustration to the output face of the substrate. This system does not use a hologram, requires a deformable surface, and, operates on the principle of total internal reflection.

Thus there is a great need in the art for an improved method and apparatus for producing high-contrast images of the surface topography of objects, such as finger and foot surfaces, while avoiding the shortcomings and drawbacks of prior art systems and methodologies.

OBJECTS AND SUMMARY OF THE PRESENT INVENTION

Accordingly it is a primary object of the present invention to provide a compact device which yields high contrast and high resolution images of the topography of an object, which images contain little or no aberrations or distortions.

A further object of the present invention is to provide a means for detecting and/or recording images of the topographical surface structure of objects.

A further object of the present invention is to allow the object to be illuminated by incoherent or coherent light.

A further object of the present invention is to create object images with sufficient detail to not only differentiate between object ridges and valleys, but to provide image details of object artifacts, such as in fingerprints.

A further object of the present invention is to provide such a system in the form of an alternative component fingerprint imaging and detection device, capable of high contrast imaging of finger pores and/or valley artifacts.

A further object of the present invention is to provide such a device for biometric identification applications, wherein further detail not achievable with prior art methods is achievable so that a smaller target area can be used for personal identification by matching not only ridge/valley differences or minutiae, but other unique details such as pore location and size as well.

A further object of the present invention is to provide a novel method of producing and detecting images of topographical surface structure associated with fingerprints.

A further object of the present invention is to provide a holographic optical element for use in a compact topographic object imaging and detection (i.e., sensing) system.

A further object of the present invention is to provide a holographic optical element for use in a compact fingerprint imaging and detection (i.e., sensing) system.

A further object of the present invention is to provide a novel method of image detection that may be applied to a broad range of objects whose features are desired to be inspected, imaged, detected, recorded, and/or compared to previously recorded object data.

Another object of the present invention is to provide a hand-held instrument for producing, viewing, displaying, storing and/or processing images of topographical surfaces.

In accordance with the general aspects of the present invention, a novel topographical image detection device is provided.

The device of the present invention includes a light source, a light transmitting substrate, a slanted-fringe type light diffractive grating and a detection system. The light diffractive grating may be embodied within holographic or non-holographic structures having a volumetric extent. The device further includes a planar object illuminating region for illuminating and/or supporting an object, such as a finger, palm, or foot surface, having topographical surface structure. The light produced from the light source enters the light transmitting substrate, travels therethrough, strikes the slanted fringe light diffractive grating at an oblique angle, and is diffracted thereby with substantial efficiency into the first diffraction order of the light diffractive grating. The diffracted light rays travel in the direction of the object illuminating region of the light transmitting substrate. Light is reflected from the substrate/air interface and passes back through the light transmitting substrate, through the slanted fringe light diffractive grating, and can be seen as a glare by a light receiving means, such as an eye, an electronic image detector, or a film recording camera. Object information captured by an electronic image detector may be stored in a computer for analysis or comparison to other objects.

When an object, such as a finger is brought in proximity with the object illuminating region of the device, which may or may not be in contact with the light transmitting substrate in embodiments, the illuminating light rays are absorbed or otherwise scattered from the finger ridges pressed up against the object illuminating region. This interrupts the aforementioned light glare and produces a light field containing a high contrast image of the fingerprint. The image is then transferred along a new optical axis, slightly shifted from the optical axis of the light illuminating the finger, through the light transmitting substrate and light diffractive grating, and onto the image detection or recording medium. The image detection medium may be realized as a system comprising an objective lens and an electronic array detector such as are commonly made as CCD or CMOS devices; an eye; a holographic recording medium or a film-type camera By creating a slight shift in axis between the illumination and detection systems, we have discovered that higher light efficiency and contrast can be obtained than with the severely shifted axes common in the prior art, or with a retroreflective type axial system. Notably, portions of the finger contacting the object illuminating region of the device appear as dark regions in the produced fingerprint image, whereas non-contacting regions appear as light regions in the fingerprint image.

The geometrical dimensions of the fingerprint image sensing device of the present invention can be made extremely compact so as to fit within a thin package, such as a PCMCIA card with all of the above-described functions embodied therein, for use in diverse applications.

These and other objects of the present invention will become apparent hereinafter and in the claims.

BRIEF DESCRIPTION OF THE DRAWINGS

For a more complete understanding of the Objects of the Present Invention, the following Detailed Description of the Illustrative Embodiments should be read in conjunction with the accompanying Drawings wherein:

FIG. 3c is an alternative first illustrative embodiment to FIG. 3a, wherein a narrow wavelength bandpass filter is added to the detection system.

FIG. 3d is an alternative first illustrative embodiment to FIG. 3b, wherein a narrow wavelength bandpass filter is added to the detection system.

FIG. 3e is a further alternative first illustrative embodiment to FIGS. 3a through 3d wherein a transmission type slanted fringe grating is substituted for the reflection type slanted fringe grating shown in FIGS. 3a through 3d.

FIG. 4 is a schematic diagram of topographical image detector of the second illustrative embodiment of the present invention, in which a first slanted fringe light diffractive grating is realized in a volume hologram affixed to a light transmitting substrate, which directs light to a second slanted fringe light diffractive grating which in turn directs light to the object to be examined;

FIG. 5 is a schematic diagram of topographical image detector of the third illustrative embodiment of the present invention, in which illuminating light enters the light transmitting substrate through an input coupling hologram attached to the face of the substrate and totally internally reflects within the substrate before illuminating a second slanted fringe diffractive grating, which redirects the light entering it to illuminate the object being examined;

FIG. 6a is a perspective view of the topographical image detector of the fourth illustrative embodiment of the present invention, in which substantially monochromatic light and a reflection-type volume hologram embodying a slanted fringe light diffractive grating are used to illuminate the object illuminating region of the light transmitting substrate, while an image detector proximate to, or affixed to the light transmitting substrate is used to detect the image of the topographical pattern of the illuminated object positioned substantially along the optical axis of the image detector;

FIG. 6b is a cross-sectional view of the topographical image detector of FIG. 6A;

FIG. 6c is a further embodiment of FIG. 6B wherein a narrow wavelength bandpass filter is added to the detection system.

FIG. 7a is a perspective view of the topographical image detector of the fifth illustrative embodiment of the present invention, in which substantially monochromatic light and a transmission-type volume hologram embodying a slanted light diffractive grating are used to illuminate the object illuminating region of the light transmitting substrate, while an image detector proximate to, or affixed to the light transmitting substrate is used to detect the image of the topographical pattern of the illuminated object;

FIG. 7b is a cross-sectional view of the topographical image detector of FIG. 7a;

FIG. 11 shows an optical arrangement for recording slanted-fringe light diffractive gratings within transmission-type volume holograms used in the construction of topographical image detectors of the present invention.

FIG. 12 shows an alternative optical arrangement for recording slanted-fringe light diffractive gratings within reflection-type volume holograms used in the construction of topographical image detectors of the present invention;

FIG. 15 is a schematic diagram of the topographical image detector of the ninth illustrative embodiment of the present invention, in which a light transmitting superstrate is arranged to support an object such as a finger, a reflection-type volume hologram embodying a slanted-fringe light diffractive grating is affixed to the underside of the light transmitting superstrate, and a light transmitting substrate used during the recording of the volume hologram is affixed to the underside thereof;

FIG. 15A is an optical arrangement for recording the slanted-fringe light diffractive grating in the volume hologram used in the ninth embodiment of the topographical image detector of the present invention shown in FIG. 12;

FIG. 16 is a schematic diagram of the topographical image detector of the tenth illustrative embodiment of the present invention, in which a reflection-type volume hologram embodying a slanted-fringe light diffractive grating is disposed between an object supporting layer and a light transmitting substrate, and is illuminated from the phase-conjugate direction by virtue of total internal reflection between the reflection-type volume hologram and an index discontinuity layer disposed between the object supporting layer and the reflection-type volume hologram;

FIG. 17 is a schematic representation of a first illustrative embodiment of the hand-supportable instrument of the present invention capable of capturing images of topographical surfaces (e.g., skin tissue);

FIG. 18A is a perspective view of a second illustrative embodiment of the hand-supportable instrument of the present invention for capturing images of topographical surfaces; and FIG. 18B is a n elevated front view of a second illustrative embodiment of the hand-supportable instrument of the present invention shown in FIG. 18A.

DETAILED DESCRIPTION OF THE ILLUSTRATIVE EMBODIMENTS OF THE PRESENT INVENTION

Referring to the figure drawings of FIGS. 1 through 16, the topographical surface imaging and detection system of the present invention will now be described in great detail. It is to be understood that all Figures contained herein are purely representative. The scale factors of the parts and from part to part, and angles of reflection, refraction and diffraction, are shown for instructional and illustrative purposes only and are not necessarily in proper absolute or relative scale.

For purposes of illustration, the illustrative embodiments of the present invention will consider imaging the topographical surface of objects such as fingers, and palms, known as fingerprints and palmprints. However, it is understood that topographical surfaces of other types of objects may be imaged with high contrast and resolution using the method and apparatus of the present invention.

Overview Of The Architecture Of The Topographical Surface Imaging and Detection System Hereof In copending Patent application Ser. No. 08/394,470, assigned to ImEdge Technology, Inc., a slanted fringe diffraction grating, typically embodied as a hologram, was used as the primary component of a compact system to produce and detect high contrast images of the surface topography of objects. In that application, the object, such as a finger, the light exiting from the slanted fringe grating illuminating the object, and the detector were all aligned about the same mechanical and optical axis. The internal structure of this system is shown in FIG. 1.

The configuration shown in FIG. I utilizes the principle of frustrated reflection to achieve a contrast difference between ridges and valleys on the object (e.g., fingerprint or skin tissue sample) being examined. Prism based systems which are typically used in the art of electronic fingerprint capture typically use a different functional concept, the principle of frustrated total internal reflection. The frustrated reflection system allows more object detail to be seen, particularly in the valley areas.

Figure 1:
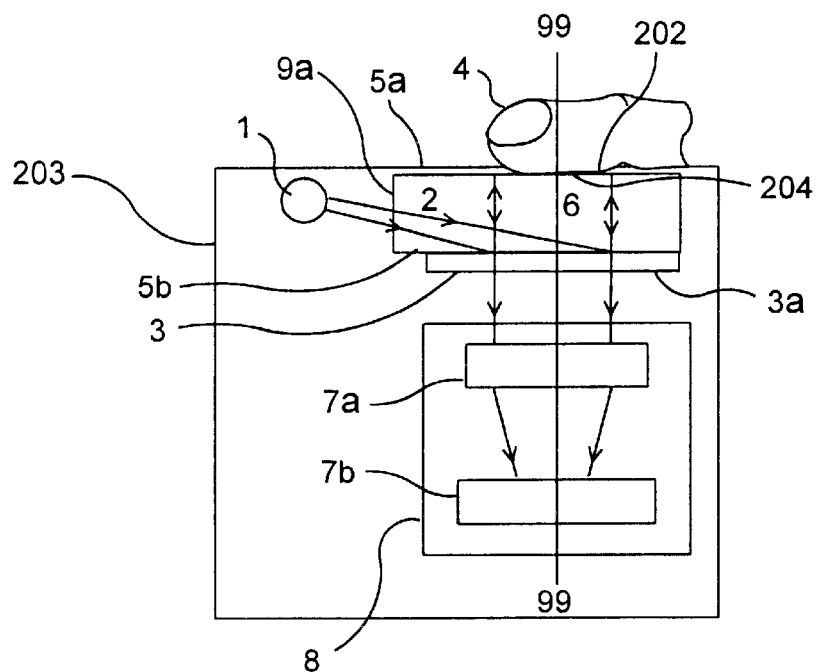
FIG. 1 is a schematic diagram of the topographical image detector previously described by the inventors, in which a slanted fringe light diffractive grating is coupled to a compact light transmitting substrate and wherein the light illuminating the object and the image light returning from the object follow substantially the same optical axis.

Referring now to FIG. 1, the previously described invention has a configuration that includes a light source 1, which may include beam reshaping optics, which emits light that enters substrate 2 in such a way as to allow light from light source 1 to travel at an oblique angle within substrate 2. Affixed to face surface 5b of substrate 2 is a volume reflection type slanted fringe grating 3. Grating 3 may be made via holographic or other means. For simplicity, it will be referred to herein as a hologram. Light from light source 1 travels through substrate 2 at an oblique angle to strike hologram 3. Hologram 3 diffracts the light impinging on it. Diffracted light is directed by the hologram to travel with its optical axis approximately normal to the face 5a of substrate 2, through region 6. Light diffracted by the hologram and reflected by face 5a is seen as "glare" by detection system 8. Finger 4 is placed through opening 202 in housing 203 and pressed onto the planar supporting region 204 of face 5a of substrate 2 within the boundaries of region 6 containing the diffracted light field. The ridges and other details of finger 4 interrupt the glare field causing a high contrast fingerprint image to occur. The fingerprint image from finger 4 is reflected back through substrate 2 and hologram 3 and is collected by detection system 8 which is substantially aligned along optical axis 99. If perfect retroreflective alignment occurs between the light source, the hologram fringe planes and substrate surface 5a, then, depending on the hologram efficiency, some reflected light will be rediffracted by the hologram an travel back toward the light source, and some light will pass through the hologram to be captured by the detector. However, it should be noted that as the angle of incidence of the construction and reconstruction light with respect to face 5b of substrate 2 approaches 90 degrees, the angular and wavelength bandwidth of the hologram become quite small, thus a small misalignment off of the retroreflective condition, which may be on the order of a degree, can cause the return light to be sufficiently far from the Bragg angle of operation of the hologram, so that a substantial amount of light reflected from face 5a, which carries the modulation information about the object, is transmitted to the detector.

One of the key elements of the above described system shown in FIG. 1 is that the finger, hologram, and detector are substantially aligned along the same axis, 99. However, in some cases, for example, for mechanical reasons, or to minimize unwanted noise, or to change the image contrast, it may be advantageous to have the finger axis and the detector axis offset slightly from each other. Additionally, this offset configuration minimizes losses from light which, in the single axis retroreflective configuration, would be reflected to the finger, and re-diffracted by the hologram towards the light source. This light is lost (although it does carry information), and never reaches the detector.

Figure 2:
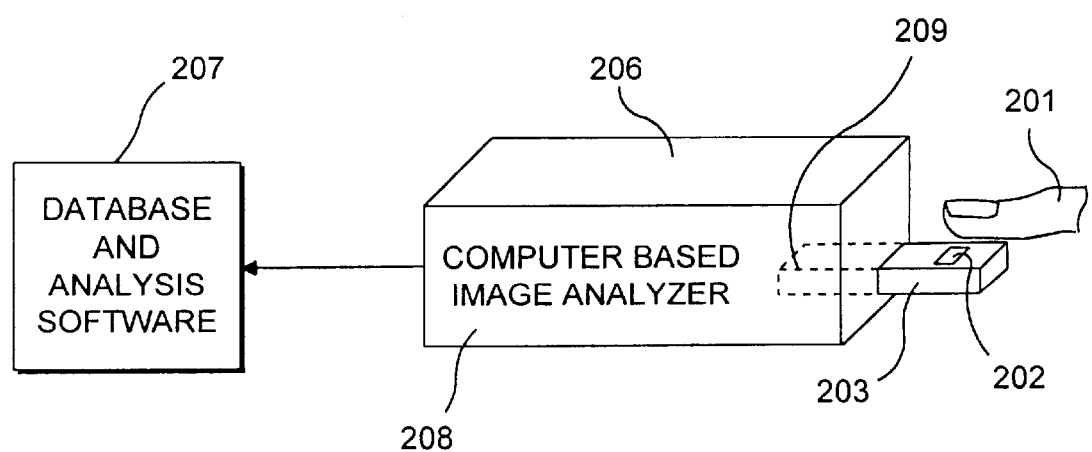
FIG. 2 is a perspective view of the topographical image capture, analysis and storage system of the present invention, showing the various integrated system components thereof, namely its topographical image detection subsystem, computer-based image analyzing subsystem, input/output interface circuitry, and archive image database subsystem.

As shown in FIG. 2, the topographical surface imaging and detection system of the present invention comprises a number of subcomponents, namely: topographical image detector 203, computer-based image analyzer 206, and archive image database 207. A person uses the system by placing his or her finger 201 through opening 202 formed in imaging system housing 203. Opening 202 provides access to planar object (i.e., finger) illuminating region 204 which is realized as a portion of planar substrate 2, as shown in FIG. 2, or cover plate 5, as shown in subsequent figures. Preferably, the fingerprint image is captured by an electronic detector 205, which may be realized, for example, as a CCD or CMOS image detection array, located within housing 203. Collectively, the image detector 203 and all its associated components can be referred to as a fingerprint image sensor. The signal from the detector 205 is electronically fed to computer based image analyzer 206 within housing 208, by way of input/output (I/O) interface circuitry 209. Notably, housing 208 may be different than housing 203. The pixellated data set corresponding to the detected fingerprint is then stored in computer database 207, for subsequent analysis or comparison. Alternatively, detected fingerprint images may be compared in real time to previously recorded fingerprint images in database 207 for any diverse number of identification purposes (e.g., criminology, access control, etc.). It is understood that the housings 203 and 208 are merely representative and will vary from embodiment to embodiment of the present invention.

Figure 3A:
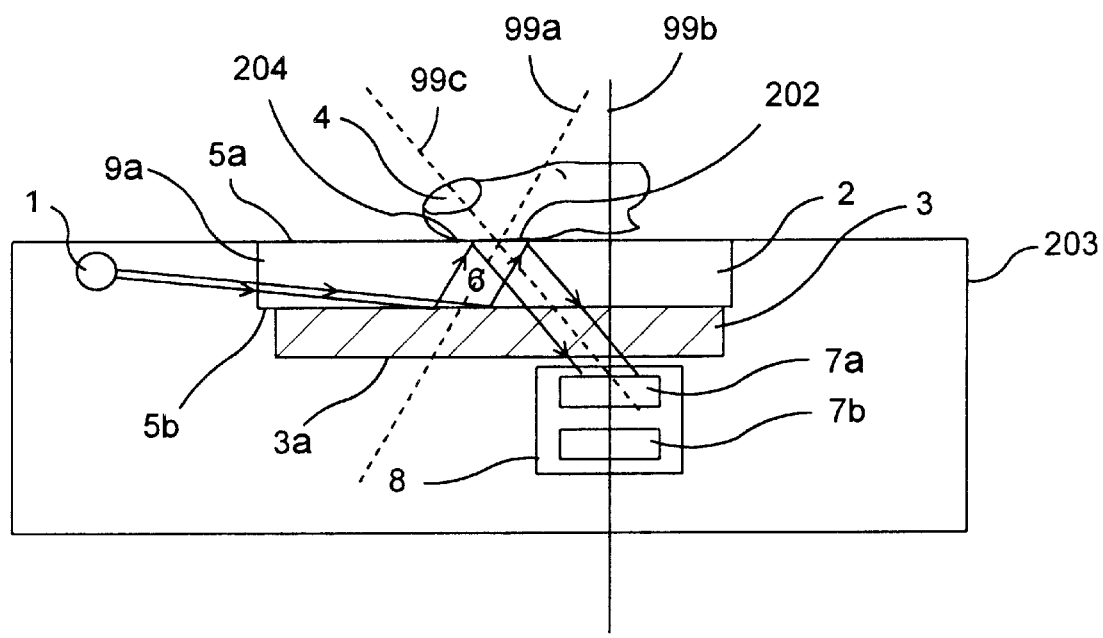
FIG. 3a is a schematic diagram of topographical image detector of the first illustrative embodiment of the present invention, in which a slanted fringe light diffractive grating is coupled to a compact light transmitting substrate in accordance with the present invention.

Referring now to FIG. 3a, the basic system and descriptions are similar to that of FIG. 1 except axis 99 is now separated into two axes. The light illuminating object 4 travels to it along axis 99a, and the light reflected from object valley/air interface 204 travels along axis 99c, which is shown distinctly different from optical axis 99a.

FIG. 3a illustrates the structure and function of the topographical surface image detection system of the first illustrative embodiment of the topographical surface image detection system of the present invention. The first embodiment of the present invention has essentially the same structure and function as that of FIG. 1, except for the change in axis between the illumination and detection functions. As shown, this embodiment of the image detection system comprises a number of subcomponents contained in compact housing 203 (not shown) namely: a light source 1 (e.g., a small tungsten or xenon lamp) which may include beam reshaping optics, for emitting a light beam; a light transmitting substrate 2 (e.g., typically less than ⅛ thick), made of an optically transparent material such as acrylic, and having an object illuminating region (i.e., surface); a reflection-type volume hologram 3 embodying a slanted-fringe type light diffractive grating, affixed to the light transmitting substrate; and an image capture system 8 in proximity with light diffractive grating 3, as shown. As illustrated, lamp 1 is placed approximately 1–2" from the substrate edge, as shown, to provide, along with image capture system 8, a highly compact construction image detection system. In alternative embodiments, lamp 1 or equivalent light source may be located remotely from the substrate 2, and coupled thereto using fiber optic elements known in the art. In typical applications, light source 1, volume hologram 3, light transmitting substrate 2, and image capture system 8 will be contained in compact housing 203 which includes opening 202 for guiding the physical placement of a finger onto the finger illuminating region of the light transmitting substrate 2.

As shown in FIG. 3a, light source 1 is arranged so that light emitted therefrom travels at an oblique angle within substrate 2. As illustrated, this is achieved by illuminating the edge 9a of substrate 2 at a slight angle off the normal to the edge. In the first illustrative embodiment, substrate 2 is bounded by face surfaces 5a and 5b and edge surfaces, 9a, b, c and d. Typically, the face surfaces have a larger surface area than the edge surfaces. During the operation of the system, the polished edge of the acrylic substrate 2 is lit by light from light source 1, such as a tungsten or xenon lamp, or a light emitting diode so as to cause a substantial amount of the input light to travel through substrate 2, and fall incident upon the slanted fringe light diffractive grating within the volume hologram 3 attached to substrate 2. This incident light diffracts into the first diffraction order of the reflection type volume hologram 3 along optical axis 99a towards the object illuminating region of the substrate. This redirected light illuminates a finger placed on the light transmitting substrate 2, reflects back along the optical axis 99c after having been spatially and intensity modulated by the topographical surface pattern (i.e., valleys and ridges) in the illuminated fingerprint. The reflected light then passes through image forming lens 7a and onto image detector 7b, both substantially aligned along optical axis 99b, to produce a high contrast fingerprint image of the illuminated finger. The operation of the image detection device will be described in greater detail with respect to the other illustrative embodiments of the present invention.

As shown, volume hologram 3 can be laminated or otherwise affixed to face surface 5b of substrate 2 either directly or indirectly by way of an additional intermediate layer or fluid or adhesive means that matches the indices of refraction between the light transmitting substrate 2 and the volume hologram 3. In the illustrative embodiment, hologram 3 comprises a recording medium embodying a previously recorded volume slanted fringe grating structure. Suitable recording media include, but are not limited to, DuPont holographic recording photopolymer, silver halide recording materials, dichromated gelatin, Polaroid DMP-128 photopolymer, etc. While holographic techniques have been used to realize the slanted light diffractive gratings used in the devices of the present invention, it is understood that other non-holographic techniques and materials may be used for producing a slanted-fringe light diffractive grating structure of acceptable definition for use in the present invention. Optionally, the recording medium of hologram 3 may be protected by a cover, 3a, composed of a transparent material. This material may be flexible, such as, for example, Mylar, or a more rigid material such as a plastic such as acrylic or polycarbonate, or glass.

In general, image detection system 8 comprises an image transfer means 7a, and an image detection means 7b. The image transfer means 7a may be realized as any device capable of transferring the image produced by the finger on surface 5a, onto the surface of the image detector 7b. Suitable devices for realizing the image transfer means 7a include the lens of an observer's eye, a lens or lens system, a lenslet array, a fiber optic array, a microchannel plate, or any combination thereof. Suitable devices for realizing the image detection means 7b include the retinal surface of a viewer's eye, a CCD image detection array, a CMOS detection array, a photographic film structure, or other suitable image capture means.

Referring to FIG. 3a, the physical operation of the first illustrative embodiment shall be described in greater detail below.

In general, light produced from light source 1 may be diverging, converging, collimated or otherwise anamorphically reshaped, depending on the enabling technology used and the product application. The produced light rays travel at an oblique angle directly through the light transmitting substrate 2, as shown in FIG. 3a, to strike the slanted-fringe light diffractive grating embodied within volume hologram 3. The slanted light diffractive grating diffracts a substantial portion of the light impinging on it into the first diffracted order, according to the well known Bragg condition $$\lambda = 2d \sin \theta$$

where $\lambda$ is the illumination wavelength of the light striking hologram 3, d is the grating fringe spacing of the volume hologram, and $\theta$ is the half angle between the object beam and the reference (or reconstruction) beam. A detailed explanation of the Bragg condition and the recording and playback of holograms and the associated well known terminology used in holography such as object, reference and reconstruction beams can be found in any of numerous books on holography, such as Practical Holography, second ed., by G. Saxby, Prentice Hall, 1994.

The light diffracted into the first diffraction order from volume hologram 3 is redirected to travel in the direction of optical axis 99a, and through object illuminating region 6. The angle at which these first order diffracted light rays travel is referenced with respect to the face 5a of light transmitting substrate 2, the optical axis of which typically approaches normal thereto, as shown in FIG. 3a. Depending on the requirements of the specific application, the light diffracted from the volume hologram may be collimated, converging, or diverging, as long as the extreme light rays travel at an angle less than the critical angle for the light transmitting substrate 2.

Figure 3B:
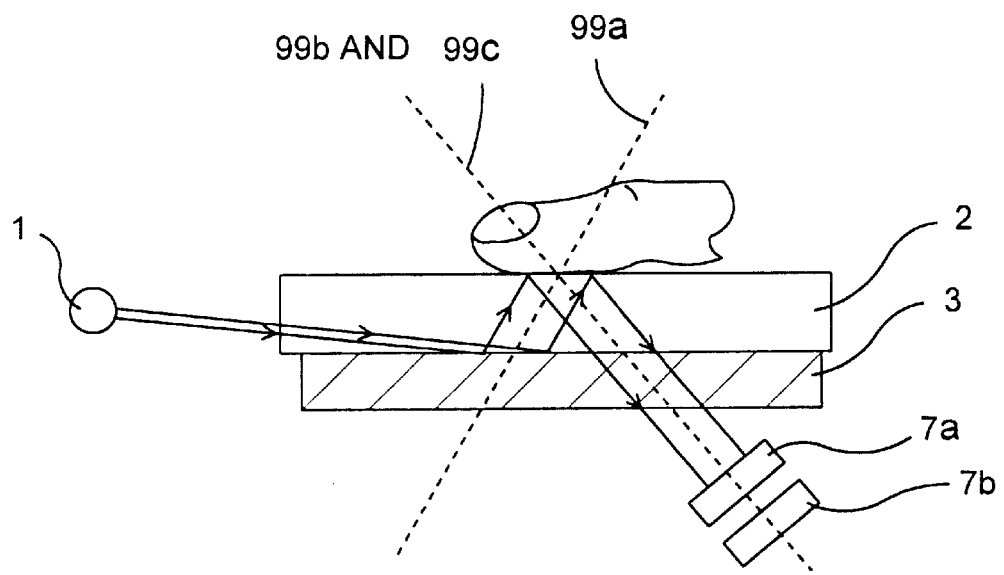
FIG. 3b is an alternative first illustrative embodiment wherein the detection system is aligned with the axis of the image light emanating from the object.

When a finger 4 is placed through opening 202 in housing 203 and pressed onto the planar illuminating region 204 of face 5a of substrate 2 within the boundaries of region 6 containing the diffracted light field, the ridges and other details of finger 4 interrupt the glare field and absorb or scatter incident light, producing a high contrast fingerprint image. If the ridges of the finger are slightly sweaty or greasy, better "index matching" to the substrate 2 will occur, producing a higher contrast fingerprint image. For dry or low contrast fingers, a small amount of grease from a nose, forehead, or a substance like petroleum jelly may be used on the finger to improve contact contrast. The fingerprint image produced from finger 4 is reflected back substantially along optical axis 99c at an angle less than the critical angle for light transmitting substrate 2 and hologram 3. Thus the light passes through light transmitting substrate 2 and volume hologram 3 and is collected by image capture system 8. Image capture system 8 is aligned along optical axis 99b which may be substantially perpendicular to surfaces 3a, 5a and 5b, as shown in FIG. 3a, or aligned substantially about optical axis 99c, which follows the central reflected ray as shown in FIG. 3b, depending on the amount by which axis 99b is offset from the center of the object, and axis 99c is tilted with respect to axis 99a. Notably, however, if a more convenient geometry is desired in any particular application, optical axis 99b or 99c of the image detection system hereof may be bent by arranging optical elements (e.g., mirrors) between the light transmitting substrate 2 and image detector 7b. Additionally, imaging system 7a in FIGS. 3a–3d may contain a prism or other optical element or elements to compensate for aberrations or distortions due to lack of coincidence between axes 99b and 99c.

Although modified somewhat by the slant angle of its fringes, the volume hologram 3 of the illustrative embodiments has filtering properties similar to standard reflection-type volume holograms having fringes aligned parallel to the recording medium. Consequently, the spectral wavelength of light rays diffracted from volume hologram 3 are within a narrow wavelength bandwidth along a portion of the electromagnetic spectrum. Thus, since the volume hologram used in the system of the illustrative embodiments of the present invention is a self-filtering device, illuminating light source 1 can be realized as a white light source, such as a tungsten halogen lamp. Alternatively, the light source can be realized by a more monochromatic source, such as an LED or a laser matched to the emission wavelength of the hologram, or tuned to a slightly different angle than the one used to construct the hologram (and thus match the Bragg condition for the particular fringe slant of the hologram). Also, since the substrate edge of the light transmitting substrate is typically long and thin, thus requiring an anamorphic beam shape for optimal light entry efficiency, the illuminating beam may be reshaped with lenses, such as a combination of spherical and/or cylindrical lenses to make more efficient use of the available light.

Preferably, light transmitting substrate 2 has an index of refraction which closely matches the index of refraction of volume hologram 3. The index of refraction of substrate 2 should typically be equal to or less than the index of refraction of hologram 3, but subject to conditions to be described later. When recording the slanted-fringe light diffractive grating within the volume hologram, the index matching criterion is particularly important to achieve properly functional diffraction efficiency, and fringe contrast. These properties can be achieved by satisfying the following condition: the thinner the substrate, or the steeper the angle of travel of the light beam within the substrate, the closer the index of refraction of the substrate and holographic recording material must match.

In an alternate embodiment, shown in FIGS. 3c and 3d, a narrow wavelength band filter, 7c, is added to the system to further improve upon contrast and signal to noise within the image. Otherwise, FIGS. 3c and 3d correspond identically to FIGS. 3a and 3b, respectively. The filter 7c typically has a central wavelength corresponding to the wavelength of the light diffracted by hologram 3. It is used to reduce adverse effects to image contrast which may arise due to such things as scattering or fluorescence from the object. FIG. 3e shows a further alternate embodiment wherein hologram 3 is a transmission hologram, rather than a reflection hologram. The basic operation of the system is otherwise the same. It is to be understood, that the filter 7c depicted in FIG. 3e may or may not be necessary, depending on system details and performance, and the axis 99b may be made to coincide with axis 99c as shown in the previous figures.

The key characteristic of operation of the slanted fringe grating which redirects incoming light to illuminate the topographic object is that the light passes from a light transmitting substrate into the slanted fringe grating. Before the light passes from the substrate to the grating, the light travels within the substrate at an angle greater than the critical angle for the substrate.

If desired or required, alternate means may be used to cause light emitted from light source 1 to enter light transmitting substrate 2 and travel therewithin at an oblique angle directly towards the slanted fringe light diffractive grating. FIG. 3a–3d demonstrate such injection of light into substrate 2 by passing light through the substrate edge. Additionally, for example, the edge 9a of the light transmitting substrate 2 may be beveled in order to change the angle of entry of the light beam from light source 1. Alternatively, the light may be forced to enter the light transmitting substrate by way of face surface 5a or 5b, as shown in FIG. 4 and 5 using, for example, a prism, a diffraction grating, or a hologram separate and apart from volume hologram 3. Other optical configurations will be apparent to those skilled in the art of optical design.

Referring now to FIGS. 4 and 5, the second and third illustrative embodiments of the image detection device of the present invention will be described. These devices of these illustrative embodiments are similar to the device of the first illustrative embodiment, except for the geometry of the light transmitting substrate and the manner in which illuminating light is coupled thereto. For illustration purposes, only one configuration of the detection system is shown in FIGS. 4 and 5, but the alternate configurations shown in FIGS. 3a–3d apply to FIGS. 4 and 5 as well. While FIGS. 4 and 5 show two possible alternative substrate geometries, it is understood that those skilled in the art of optical design will readily derive other ways of injecting light into the substrate so that it travels through the light transmitting substrate and strikes the affixed slanted light diffractive grating at an oblique angle (i.e., grazing incidence).

As shown in FIG. 4, the image detection device of the second illustrative utilizes a face lit light input coupling technique. Typically, this technique requires that the light transmitting substrate 21 be longer along its longitudinal extent. As shown, light emitted from light source 20 and conditioned by optional light conditioning optics first passes through substrate 21 and impinges on reflection-type hologram 22 embodying a slanted light diffractive grating. This volume hologram 22 is laminated or otherwise attached to substrate 21 and has an index of refraction that closely matches that of substrate 21 as noted above. If desired, hologram 22 may contain a mirrored backing to enhance the amount of light which travels into substrate 21, or an absorptive backing to minimize stray light, or no backing at all.

As shown in FIG. 4, light is diffracted by volume hologram 22 (i.e., input light coupling element) at an angle greater than the critical angle for the substrate 21 and travels within substrate 21 to directly strike the slanted light diffractive grating prerecorded in reflection type volume hologram 23, as described in the first illustrative embodiment. First order diffracted light 25, produced by hologram 23 passes through light transmitting substrate 21 along optical axis 99a to produce aforementioned glare field which is interrupted by the ridges of finger 24 placed on the object illuminating region of the light transmitting substrate. The fingerprint image produced from finger 24 passes substantially along optical axis 99c, through substrate 21, through hologram 23 and to image capture system 28, as described in FIGS. 3a–3d. In the illustrative embodiment of FIG. 4, light used to illuminate volume hologram 23 does not undergo total internal reflection within the substrate 21 before illuminating volume hologram 23. Image capture system 28 as shown is comprised of elements 26 and 27. Optical system 26 transfers the finger image to detector 27.

In FIG. 5, a third illustrative embodiment of the image detection device of the present invention is shown. Unlike the second embodiment, the third illustrative embodiment utilizes the principles of total internal reflection to deliver the light beam to the hologram. Such light guiding techniques are disclosed in U.S. Pat. No. 5,295,208 to Caulfield, et. al. incorporated herein by reference. As shown in FIG. 5, light produced from light source 10 and conditioned by light conditioning optics impinges upon the slanted light diffracting grating embodied in transmission-type slanted fringe hologram 11 which is laminated or otherwise attached to light transmitting substrate 12. This incident light is diffracted into substrate 12 at an angle greater than the critical angle for substrate 12. Consequently, the light bounces off the opposing surface by total internal reflection within substrate 12 and travels within substrate 12 to strike a slanted fringe light diffractive grating embodied within reflection-type hologram 13 . The light falling at the correct angles on volume hologram 13 is diffracted thereby and travels along axis 99a, through substrate 12 to form beam 15 whose reflection produces a glare field. The glare field which is interrupted by finger 14 placed on the illuminating region of the light transmitting substrate 12. The fingerprint image produced from finger 14 passes substantially along optical axis 99c, through substrate 12 and through volume hologram 13 and is collected by an image detection system 18 comprising a lens or lens system 16 or other means (e.g., microchannel plate or microlens array) which transfers the fingerprint image to the image detection plane of an image detector 17. As in FIGS. 3a–3d, image detection system 18 may be located along axis 99b or 99c and may contain an additional narrow wavelength bandpass filter for contrast enhancement. Note that method of injecting light into the face of substrate 2 as illustrated in the examples of FIGS. 4 and 5 applies to any of the systems with or without transfer lenses as described herein. In the examples shown in FIGS. 4 and 5 reflection holograms are depicted, however, it is to be understood that one can depict face-lit configurations that will work as well with transmission holograms for injecting light into the substrate.

Fingerprint Image Sensing Systems Without Image Transfer Lenses

In particular embodiments of the imaging and detection devices hereof, the image transfer means (e.g., lens or lens system) is eliminated from the design. In such embodiments, the light rays associated with the image formed at the interface of the finger and the surface upon which the finger is pressed must maintain their integrity over the distance from the finger to the image detector. By virtue of the fact that the image transfer lens is eliminated in such designs, the image detection device can be realized in the form of an extremely thin, compact device adapted for use with the system shown in FIG. 2. This ultra-thin geometry makes the fingerprint image sensor particularly suited for use in access control devices incorporated within portable computers, associated PCMCIA cards, cellular telephones, or other devices where minimal space for a fingerprint verification device is available. Several embodiments of this optical system design will be described in great detail below.

As shown in FIGS. 6a through 6c, the fourth illustrative embodiment of the image detection device comprises a number of subcomponents compactly integrated within the interior of an ultra compact housing about the size of a PCMCIA (cardlike) package. The general packaging is shown in FIG. 6a with interior components shown in FIG. 6b and FIG. 6c. As shown such components include: light transmitting substrate 2 having a finger illuminating region; a reflection-type volume hologram 3 affixed to the underside of substrate 2, and having a slanted-fringe light diffractive grating embodied therein; and, an image detection device 7b located proximate to or suitably affixed by way of an adhesive or index matching layer to the underside of the hologram. In an alternate embodiment, a first narrow bandpass filter panel 7c, as shown in FIG. 6c, matching the center output wavelength of the diffracted light from hologram 3, is used between the underside of the volume hologram 3 and detector 7b to improve contrast and signal to noise ratio. As shown, components 7b and 7c are substantially aligned with optical axis 99b or 99c, as described earlier for FIG. 3a–3d. Note that axes 99b and 99c may coincide. The device also includes a substantially monochromatic light source 1 (e.g., laser diode with wavelength of about 650 nm) and optional beam shaping optics, for producing a substantially monochromatic light beam tuned in wavelength or input angle to match the Bragg angle condition for grating or hologram 3. Alternatively, a white light source may be used instead of a laser. In such a case, the white light beam may be passed through a second narrow bandpass filter, 211 selected as above in order to match the Bragg condition for the slanted fringe light diffractive grating embodied within the volume hologram 3. Notably, narrow bandpass filter 7c eliminates stray light or unwanted fluorescence from the finger by virtue of its narrow pass band. Electronic I/O circuitry 212 is provided for powering the light source 1 and image detector 7b and passing information to and from image detector 7b. Such circuitry may be interfaced to an appropriate connector or connectors, located, for example, on edge 209 of housing 203 as shown in FIG. 6a. Preferably, the entire structure is housed in compact housing 203. During the operation of the illustrative embodiment, the finger is placed through opening 202 in housing 203 onto planar finger supporting region 204. The light transmitting substrate 2 and volume hologram 3 affixed thereto may comprise the protective cover plate required for the image detector 7b.

As shown in FIGS. 7a and 7b, the fifth illustrative embodiment of the imaging and detection device comprises a number of subcomponents also compactly integrated within the interior of an ultra compact housing about the size of a PCMCIA package. As shown such components include: a transmission-type volume hologram 3 having a slanted fringe light diffractive grating embodied therein; an optically transparent protective layer 215 affixed to the top surface of the volume hologram 3 and serving to provide a finger supporting surface; a light transmitting substrate 2 affixed to the underside of the transmission-type volume hologram 3; optionally, a first narrow band-pass filter panel 7c proximate to, or directly affixed to the underside of the light transmitting substrate 2 and tuned to the output wavelength of volume hologram 3; an image detection device 7b proximate to, or directly affixed by way of an adhesive or index matching layer to the underside of the hologram 3, or, if used, narrow band-pass filter 7c. As shown, components 7a and 7b are substantially aligned with optical axis 99b, as described earlier for FIG. 3a–3d. Note that axes 99b and 99c may coincide. The device also includes a light source 1, and optional beam shaping optics, for producing a substantially monochromatic light beam tuned in wavelength or input angle to match the Bragg angle condition for transmission volume hologram 3. Alternatively, a white light source 1 may be used instead of a laser. In such a case, the white light beam may be passed through a second narrow bandpass filter, 211 selected as above in order to match the Bragg condition for the slanted fringe light diffractive grating embodied within the volume hologram 3. Notably, narrow bandpass filter 7c eliminates stray light or unwanted fluorescence from the finger by virtue of its narrow pass band. Electronic I/O circuitry 212 is provided for powering the light source 1 and image detector 7b and passing information to and from image detector 7b. Such circuitry may be interfaced to an appropriate connector or connectors, located, for example, on edge 209 of housing 203. Preferably, the entire structure is housed in compact housing 203. During the operation of the illustrative embodiment, the finger of the subject to be identified is placed through opening 202 in housing 203 onto planar finger supporting region 204. Notably, as shown, in this illustrative embodiment, transmission volume hologram 3 is illuminated by light passing through the light transmitting substrate 2 into the transmission hologram 3.

In the fifth illustrative embodiment of the imaging and detection device system shown in FIGS. 7a and 7b, the fringe slant angle of the transmission hologram is generally such that the optical axis 99a of the diffracted beam travels at an angle less than the critical angle of the substrate and/or recording medium. The function and properties of such a slanted fringe transmission grating are similar to that of a reflection-type slanted fringe light diffractive grating. As such, this alternate embodiment of the image detection system of the present invention will operate in a similar fashion to the system configuration shown in FIGS. 3a–3d.

It is to be understood that in the transfer lenseless systems described herein, light from light source 1 may be injected into substrate 2 through the edge or by face lit methods, as have previously been described for systems utilizing an image transfer means.

Procedures For Designing Transfer-Lenseless Fingerprint Image Sensing Systems

When designing transfer-lenseless systems of the type described above, there is a need to ensure that the light rays returning from the elemental features in the fingerprint image (e.g., ridges, valleys, pores, etc.) formed at the surface upon which the finger is pressed are detected by the image detection system prior to being allowed to diffract (i.e., spread) too much and cause unacceptable levels of image degradation. This design concern influences (1) the maximum distance at which the image detector can be located relative to the finger/surface interface, and (2) the highest resolution attainable using a given image detector. The minimum pixel resolution required by the image detector will depend, typically, on the number of minutia or other pertinent features required by the fingerprint image matching algorithm (i.e., computer software) employed by the system. The degree of light spreading acceptable for a given application will depend on which fingerprint structures (i.e., ridges, valleys or pores) will be used by the fingerprint image matching algorithms.

For the case when the ridges and valleys of a fingerprint image must be detected at the image detector for use in the image matching process, a geometrical optics model can be developed for the image sensor (e.g., shown in FIGS. 6 or 7) and then the laws of Fresnel Diffraction in the near field are applied in a conventional manner. From such modeling, a mathematical expression can be derived for describing the fingerprint image capture process where, for example, a collimated monochromatic laser light beam (i.e., emanating from the holographic grating hereof) is reflected/scattered from a square region on the finger, having side dimensions W, and will travel a distance $1_F$ equal to about one Fresnel number (Fresnel length) before diverging. This distance is given approximately by the expression $$l_{Fc} \approx \frac{w^2}{5\lambda}$$

where $\lambda$ is the wavelength of the light in the medium.

It is known that the width of fingerprint ridges is typically in the range of 100 microns to 300 microns and the spatial period of a typical ridge-valley cycle is about 350 microns. Thus, for example, if the distance between adjacent ridges is conservatively deemed 250 nm, and the image light rays pass through air, then the above expression predicts that the image light rays will travel a distance of about 19 mm before spreading appreciably. Thus, if a hologram (made using the 647 nm line from a Krypton laser) is laminated directly onto an acrylic substrate of ⅛" thick, and replayed by a laser diode, emitting a wavelength of 650 nm, we have discovered that the image detector can be easily placed next to the hologram without requiring an image transfer lens to transfer the image from the finger plane to the image detector.

In the case of imaging fingerprint pores, typically having sizes in the range of 60 microns to 250 microns, the above design procedure will involve some additional considerations. Based on the above equation, the image of a 60 micron pore would not spread appreciably for a distance of 1.1 mm. Therefore, if absolute pore size is important in the image, using a thinner substrate (e.g., ¹⁄₃₂" thick) would be more appropriate. When thicker substrates are used, the image of the pores becomes disproportionately large as a result of Fresnel diffraction. When using a pore-based recognition algorithm, analyzing the relative pore size and location may actually be helpful, as the Fresnel diffraction of the light emanating therefrom makes the pores easier to detect. The image of large pores, however, can render analysis of ridge-valley modulation difficult in such regions. It has been found that for a fingerprint capture device fitting into a form factor the size of a PCMCIA card, having a maximum thickness of 6–12 mm, the diffraction spread of feature sizes over 150 microns does not appear to be of significant concern.

At distances greater than about two Fresnel lengths, the width of the image increases according to the following approximate formula $$w_I \approx w + \left(\frac{4.88\lambda}{w}\right)d$$

where $w_I$ is the width of the image at a distance d from the starting (aperture) plane. It can be shown that for various feature sizes, the image grows according to the above expression as viewed from several distances, for an illumination wavelength of 650nm. As a result, measurement of pore size may be unreliable for small to medium size pores since it may be difficult to distinguish between a small pore whose image has spread due to diffraction, and a larger pore, with an equivalent image size. Consequently, pore based recognition systems realized in very thin packages with no image transfer lens must rely on features such as pore location and shape.

Fingerprint Image Sensing System Using Cross Polarization Filtering Techniques

Figure 8:
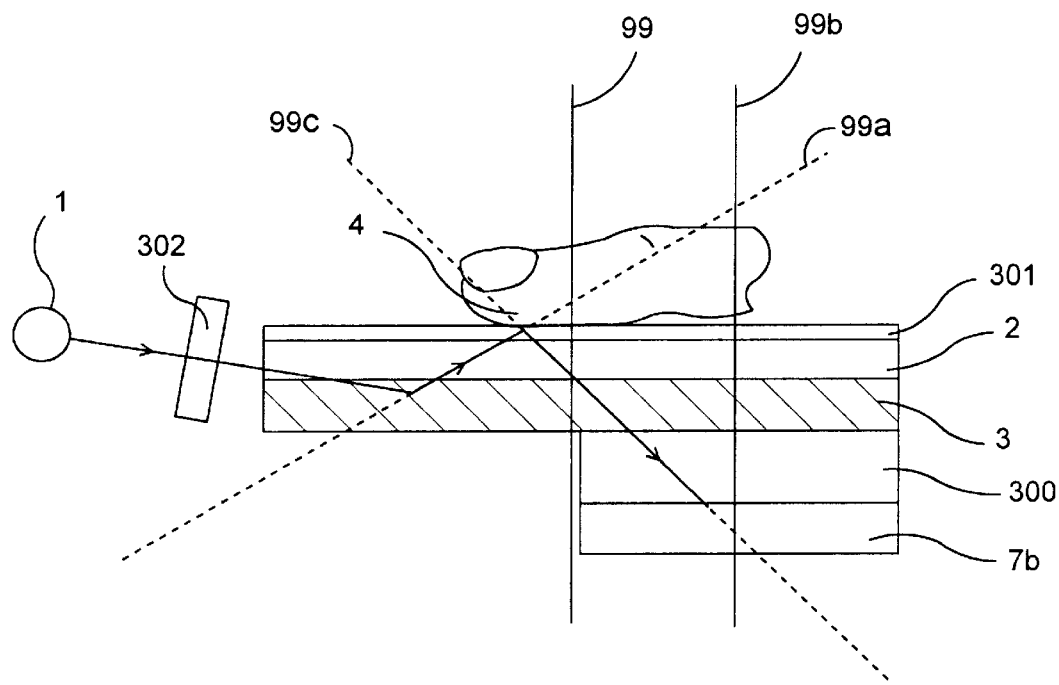
FIG. 8 is a cross-sectional view of the topographical image detector of the sixth illustrative embodiment of the present invention, employing cross-polarization techniques to improve the image contrast and signal-to-noise ratio of the detector.

In FIG. 8, a sixth embodiment of the fingerprint imaging and detection system hereof is shown. As will be described below, this embodiment of the system employs cross-polarization techniques in order to block out stray light and spatial noise in order to markedly improve the image contrast and signal-to-noise ratio of the system. In general, the cross-polarization techniques employed in this embodiment of the present invention can be used in conjunction with any of the reflection-type volume holograms, or transmission-type volume holograms as disclosed in any of the embodiments herein. Also, this technique may be used in a fingerprint image sensing system with or without an image transfer lens. A narrow bandpass filter as previously described herein may also be used in conjunction with the cross-polarization system. Additionally, the cross-polarization system may be used with a monochromatic light source or a white light source whose light output is or has been made linearly polarized. For illustrative purposes only, this aspect of the present invention will be described in a system employing a slanted-fringe reflection-type hologram, avoiding the use of an image transfer lens, as taught in FIGS. 6 and 7.

As shown in FIG. 8, the sixth illustrative embodiment of the imaging and detection device comprises a number of subcomponents compactly integrated within the interior of an ultra compact housing about the size of a PCMCIA package. As shown such components include: light transmitting substrate 2 having a finger illuminating region; a reflection-type volume hologram 3 affixed to the underside of substrate 2, and having a slanted-fringe light diffractive grating embodied therein; and a thin P-polarizing filter panel 300 (i.e., "an analyzer") proximate or directly affixed to the underside of the volume hologram 3 for transmitting only P-polarized light components; a quarter-wave phase retardation plate 301 proximate to or directly affixed to the upperside of the light diffractive grating, for producing circularly polarized light rays from S-polarized light rays diffracted from hologram 3 and directed to the finger; and an image detection panel 7b proximate to or directly affixed by way of an adhesive or index matching layer to the underside of the polarization filter 300. As shown, elements 2,3, and 301 are substantially aligned with optical axis 99b. Elements 300 and 7b are aligned with axis 99b, which may coincide with axis 99c, as described earlier for FIG. 3a–3d. The device also includes a substantially monochromatic light source 1, an S-polarizing filter 302, if the light source is unpolarized, and optional beam shaping optics, for producing a substantially monochromatic light beam tuned in wavelength or input angle to match the Bragg angle condition for grating or hologram 3, and having an S-polarization state. As in FIG. 7a, electronic I/O circuitry 212 is provided for powering the light source 1 and image detector 7b and passing information to and from image detector 7b. Such circuitry may be interfaced to an appropriate connector, or connectors, located, for example, on edge 209 of housing 203. Preferably, the entire structure is housed in compact housing 203. During operation of this illustrative embodiment, the finger is placed through opening 202 in housing 203 onto planar finger illuminating region 204. The light transmitting substrate 2 and volume hologram 3 affixed thereto may comprise the protective cover plate required for image detector 7b.

In the sixth illustrative embodiment, the holographic grating 3 is designed to have particular light diffraction efficiency characteristics. In particular, the light diffraction efficiency of the hologram to light incident the surface adjacent the fingerprint to be imaged (i.e., in the direction normal thereto) is minimized for P (linearly) polarized light rays, whereas in the same direction the light diffraction efficiency is maximized for S-polarized light rays. In this embodiment, S-polarized light rays are used to illuminate the holographic light diffractive grating. S-polarized light rays diffracted from the hologram pass through the quarter-wave plate and become circularly polarized. Circularly polarized light scattered and reflected from the fingerprint passes through the quarter wave plate and becomes linear again, this time P-polarized As the light diffraction efficiency of the holographic light diffraction grating is minimized for P-light rays propagating in the direction normal to the grating surface, towards the image detector, stray light and spatial noise are precluded from transmission towards the image detector, improving the contrast and signal-to-noise of the system. The optional image analyzer 300 can be interposed between the holographic light diffraction grating and the image detector in order to further block out stray light and light spatial noise from light rays scattered at the interface of the fingerprint and quarter wave plate. In this fingerprint imaging and detection system, an image transfer lens system and/or additional narrow wavelength band filter may or may not be used depending on the application at hand.

Functional Mechanism of Previous Embodiments

The previously described embodiments are based on the principle of frustrated reflection. Light is reflected at the substrate/valley interface and returns through the substrate according to the standard laws of reflection. Light at the substrate/ridge interface is absorbed or scattered. The image detected has dark ridges and bright valleys. In the design of these systems, the slanted fringe diffraction gratings as described herein have a very narrow angular bandwidth of operation. For example, according to the well known coupled wave theory of volume hologram operation, as has been described by Kogelnik (*Bell System Technical Journal,* V 48, N 9, p.2909ff) if a slanted fringe grating is made using a Krypton laser at 647 nm, in a recording medium with an index of refraction of 1.5, a fringe modulation of 0.03 and a slant angle of 44 degrees, the FWHM angular bandwidth of operation of the hologram will be around 1 degree. Therefore if a reflected ray from the substrate/valley interface were to have a 1 degree angular offset from true retroreflection, the ray would pass through such a slanted fringe grating with high transmission efficiency. If the detector were as far as 6 millimeters from the finger, the optical axis change from the axis of the light striking the finger to the axis of the light reflected back from the substrate/valley interface would represent a shift of the detector of around 0.1 millimeters, a negligible amount to a typical detector of, say, ⅓" size. Thus with high efficiency of the hologram, and a detection optical axis slightly offset from the object illumination axis, a high contrast image can be achieved with the system disclosed herein.

An additional advantage of such a frustrated reflection system over a system utilizing frustrated total internal reflection is that with the frustrated reflection system, valley artifacts and other details can be imaged. This is not the case with frustrated total internal reflection based systems.

Tir-Based Fingerprint Image Sensing System

Figure 9A:
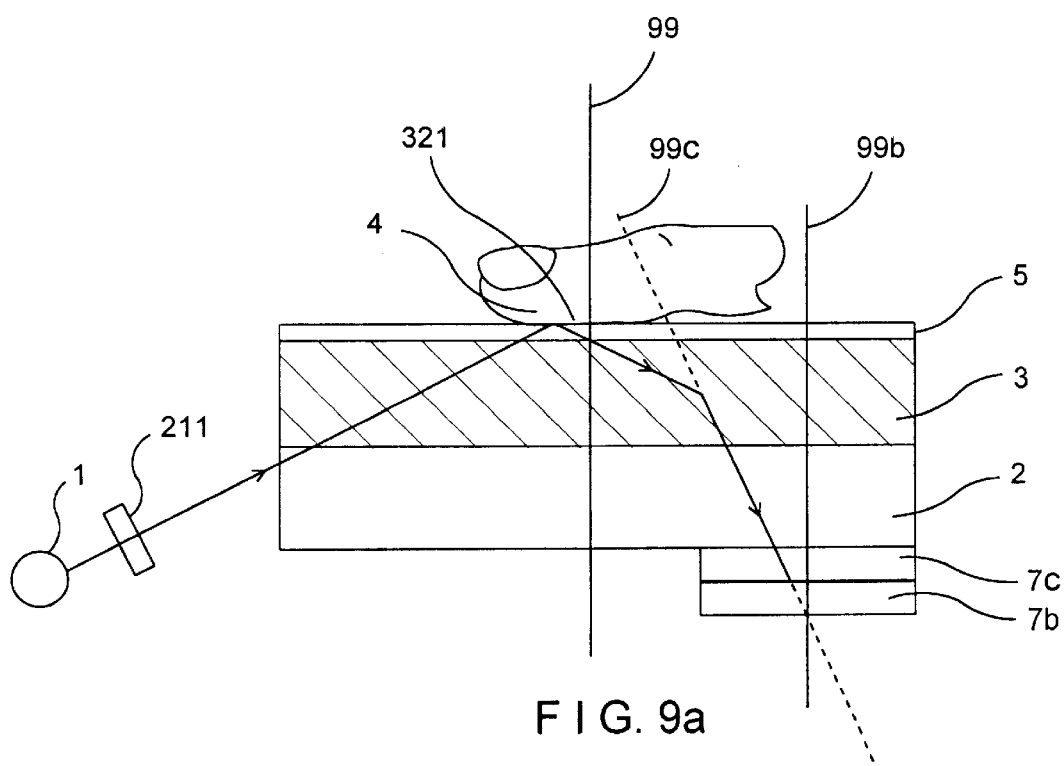
FIG. 9a is a cross-sectional view of the topographical image detector of the seventh illustrative embodiment of the present invention, employing the principle of total internal reflection in conjunction with a slanted fringe light diffractive grating, to form fingerprint images for detection.

In FIG. 9a, a seventh embodiment of the fingerprint imaging and detection system is disclosed. This embodiment of the present invention is based on total internal reflection (TIR) principles. In general, the TIR technique employed in this embodiment of the present invention can be used in conjunction with reflection-type volume holograms as shown in FIGS. 6, or with transmission-type volume holograms as disclosed in FIGS. 7. Also, this technique may be used in a fingerprint image sensing system with or without an image transfer lens, a narrow band filter system, and/or a cross-polarization system as previously described herein. For illustrative purposes only, this aspect of the present invention will be described in a system employing a slanted-fringe volume-type hologram, avoiding the use of an image transfer lens, as taught in FIGS. 6 and 7.

As shown in FIG. 9a, the seventh illustrative embodiment of the image detection device comprises a number of subcomponents compactly integrated within the interior of an ultra compact housing about the size of a PCMCIA package. As shown, such components include: light transmitting substrate 2 having a finger illuminating region; a transmission-type volume hologram 3 affixed to the upper side of substrate 2, and having a slanted-fringe light diffractive grating embodied therein; optionally, a first narrow band-pass filter panel 7c proximate to, or directly affixed to the underside of substrate 2 and tuned to the output wavelength of volume hologram 3; an image detection panel 7b directly proximate to or affixed by way of an adhesive or index matching layer to the underside of the narrow band-pass filter, if it exists, or to the substrate if the filter is not used; and a thin, protective panel 320 of transparent material such as glass or plastic, disposed upon the upper surface of the holographic grating 3. As shown, elements 2, 3 and 320 are substantially aligned with optical axis 99. Elements 7a, b and c are substantially aligned with axis 99b or 99c, as described earlier for FIG. 3a–3d. Note that axes 99b and 99c may coincide. The device also includes a substantially monochromatic light source 1 and optional beam shaping optics, for producing a substantially monochromatic light beam tuned in wavelength or input angle to match the Bragg angle condition for grating or hologram 3. Alternatively, a white light source may be used instead of a laser. In such a case, the white light beam may be optionally passed through a second narrow band-pass filter 211 selected as above in order to match the Bragg condition for the slanted fringe light diffractive grating embodied within the volume hologram 3. Notably, narrow band-pass filter 7c eliminates stray light or unwanted fluorescence from the finger by virtue of its narrow pass band. This system may be contained in a package similar to that of FIG. 7a. Electronic I/O circuitry 212 is provided for powering the light source 1 and image detector 7b and passing information to and from image detector 7b. Such circuitry may be interfaced to an appropriate connector, or connectors, located, for example, on edge 209 of housing 203. Preferably, the entire structure is housed in compact housing 203. During operation of this illustrative embodiment, the finger is placed through opening 202 in housing 203 onto planar finger illuminating region 204. The light transmitting substrate 2 and volume hologram affixed 3 thereto may comprise the protective cover plate required for image detector 7b.

Figure 9B:
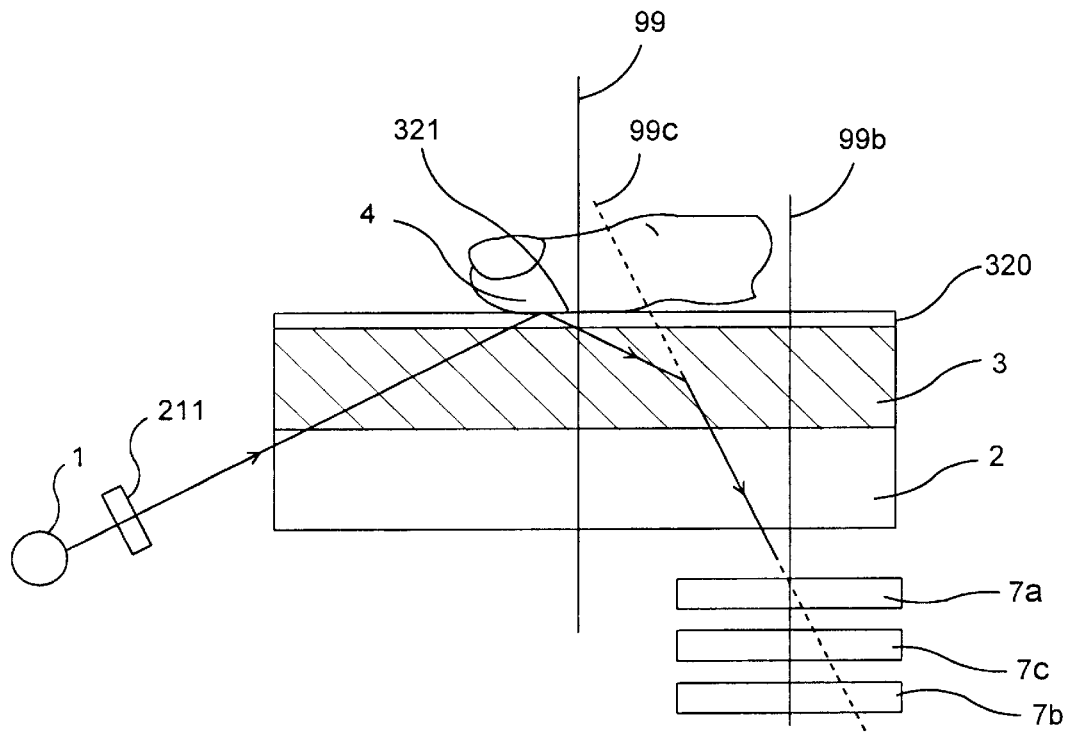
FIG. 9b is a alternate embodiment to FIG. 9a wherein an image transfer means is used to transfer the image of the object to the detection system.

Additionally, in an alternate embodiment of the seventh embodiment, as shown in FIG. 9b, a transfer lens system 7a may be used to image the object image onto detector 7b. In FIG. 9b, optional filter 7c may be placed between lens system 7a and detector 7b, as shown, or between substrate 2, and lens system 7a.

In the seventh embodiment of the image detector hereof, the reference (i.e., r reconstruction) light beam from light source 1 passes through the substrate, enters the holographic grating off Bragg, passes through the hologram and impinges on finger-hologram interface 321. Where there are valleys in the fingerprint structure, the incident light beam undergoes total internal reflection at the hologram-fingerprint interface 321. This totally-internally-reflected light strikes the slanted fringes of the hologram at the Bragg angle of the hologram and thus is diffracted in a direction along optical axis 99c. This diffracted light passes through the substrate 2 and optional filter 7c and is ultimately detected by detector 7b. Notably, to design the hologram for this particular embodiment of the present invention, a geometrical optics model should be developed comprising the following parameters: the grazing incidence angle of the incident reconstruction beam; the wavelength thereof; the fringe angle of the hologram; the fringe spacing of the hologram; and the indices of refraction of the substrate and the recording medium. From such a model, the hologram designer can then determine the conditions which must be satisfied for the device to operate according to the above-described principles.

Notably, a principal advantage of the image detection device shown in FIGS. 6 through 9a is that the absence of an image transfer means permits an ultra-compact construction.

Methods for Constructing Slanted-Fringe Holograms

Figure 10:
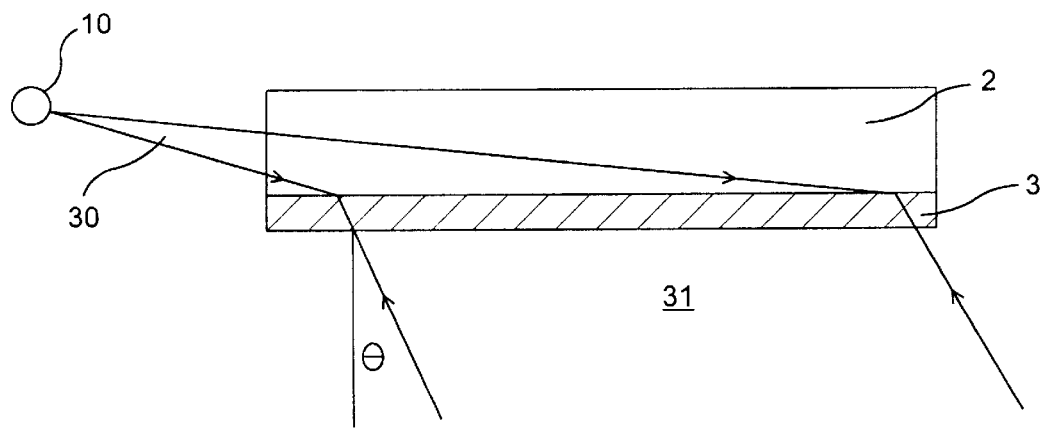
FIG. 10 shows an optical arrangement for recording slanted-fringe light diffractive gratings within reflection-type volume holograms used in the construction of topographical image detectors of the present invention.

The following holographic recording methods have been successfully practiced during the production of both light transmission and reflection holographic structures embodying slanted-fringe light diffractive gratings that have been incorporated into topographic image detection systems of the first through five illustrative embodiments of the present invention. Notably, the slanted fringe light diffractive gratings used in such devices will produce substantially collimated light rays for object illumination. The optical recording arrangements shown in FIGS. 10 through 12 are configured for producing such types of slanted fringe light diffractive gratings. However, as will be shown hereinafter with reference to FIGS. 14 through 16, it is possible to use slanted gratings that produce light rays that converge from a perspective point, as in the case of viewing objects with human vision. While reference is made to the optical recording arrangements of FIGS. 10 to 12 in the below described method, it is understood that the method is equally applicable to the production of the slanted gratings used in the eighth, ninth and tenth embodiments of the present invention shown in FIGS. 14 through 16. However, in such embodiments, the optical recording arrangements shown in corresponding FIGS. 14A and 15A would be used.

When recording the slanted-fringe light diffractive grating within the hologram 3, it is particularly important to achieve high diffraction efficiency, and high fringe contrast. It has been discovered that this can be achieved by closely matching the index of refraction of the light transmitting substrate 2 with the index of refraction of the recording medium used to make the volume hologram 3 in the illustrative embodiments. In general, there are two different cases to consider. As will be described below, each case has its own special approach to index matching.

In the first case, where the index of refraction of substrate 2 is equal to or less than the index of refraction of recording medium 3, the above-described properties can be achieved by satisfying the following condition: the thinner the substrate, or the steeper the angle of travel of the light within the substrate, the closer the index of refraction of the substrate and the recording material must match. The graph of FIG. 13 disclosed in copending U.S. patent Ser. No. 08/394,470 filed Feb. 27, 1995 illustrates the importance of the above-described index matching criterion. The set of curves associated with this graph shows the percentage of s-polarized light which will be transmitted from a substrate having an index of refraction less than 1.495 by the amount shown on the x-axis into a recording medium having an index of refraction of 1.495. Each curve represents the angle of incidence of a light wave within the substrate, as measured to the normal to the substrate. In order to achieve a compact, cost-effective system, it is desirable to utilize thin substrates, necessitating incident angles within the substrate approaching 90 degrees. This graph shows curves for arbitrarily selected steep incident angles of 85, 88, 88.5, 89, 89.5 and 89.9 degrees. These curves were derived from the well known Fresnel reflection equations combined with the Snell's Law equation, as may be found, for example, in *Optics* by K. D. Moller, University Science Books, Mill Valley, Calif., 1988, page 196. The values shown on the x-axis were arbitrarily selected to extend to 0.005, representing a refractive index of 1.490 for the substrate. It should be understood that the values indicated in were arbitrarily selected for illustration purposes, and do not represent specific physical bounding values. As can be seen from this graph, significant transmission of light into the recording medium from a thin substrate can be achieved by closely matching the index of refraction of the substrate and recording medium. For a particular grazing angle of incidence for the reference beam during recording (or reconstruction beam on playback), the graph shows how close the match must be. Clearly, the index match is functionally dependent on the incident angle of the laser beam used to record the slanted light diffractive grating.

In the second case, where the index of refraction of the recording medium is less than the index of refraction of the substrate, an evanescent wave is naturally produced at the boundary between the substrate and the recording medium. This results in limited penetration of the light beam from the substrate into the volume of the recording medium. If certain recording media are used (e.g., the DuPont family of holographic photopolymers having migratable monomer components drawn towards light), then the creation of an evanescent wave at the boundary between the recording medium and the substrate, will draw monomer to the boundary between the substrate and the recording layer. This monomer migration process increases the local index of refraction, thereby allowing the holographic recording reference beam to penetrate into the volume of the recording medium. This self-induced index matching effect enables interference of the reference beam with an object beam so as to produce recordable and permanent high-contrast slanted fringes within the recording medium. Thus when the recording medium index of refraction is slightly less than the index of refraction of the substrate, it is nevertheless possible to achieve sufficient index matching and recording of high fringe contrast in slanted light diffractive gratings.

Having addressed index matching requirements, the holographic recording procedure will now be described in detail below. The first step of the holographic recording procedure hereof involves cutting a piece of DuPont holographic recording film material (designated HRF 352 having index of refraction at the sodium D line of approximately 1.506) into a 2 inch square. Then using a roller pressure technique, the square is laminated to a piece of BK10 glass whose edges were polished to an optical finish. Notably, these materials are index matched in accordance with the above-described method. The resulting structure, having approximately a half inch thickness and an index of refraction at the sodium D line of 1.498, was used as the recording substrate. Using the optical arrangement shown in FIG. 10, the film material was exposed to Argon laser light at 514.5 nm using s polarization and other well known and standard holographic recording techniques. The angle of incidence of the reference beam within the glass substrate, was approximately 88 degrees. The film was exposed to approximately 500 mJ/cm2. The details of the recording arrangement are described below in connection with the recording of reflection holograms.

As shown in FIG. 10, the reference beam 30, which may be collimated, converging or diverging, or otherwise anamorphically shaped, depending on the application and how the reconstruction illumination is to be shaped, is fed through the edge of substrate 2. Alternatively, the reference beam may also be fed from the face as discussed previously. The reference beam then travels within the substrate and impinges on holographic photosensitive medium 3 laminated to substrate 2. The object beam, 31, while depicted in FIG. 10 as being diverging, may also be converging or collimated, depending on the application. This beam 31 impinges on holographic recording medium 3 with an optical axis, such that the reconstructed first order diffraction beam will travel at an angle with respect to optical axis 99c, as described in the previous embodiments, about or less than the critical angle for the substrate and/or recording medium, as shown. The side that the object beam strikes holographic recording medium 3 depends on the final application, and determines whether the hologram will be reflection hologram (as shown in FIG. 10) or a transmission hologram (as shown in FIG. 11). The interference of the two beams within the volume of the holographic recording medium 3 expose the same.

If the diffracted illumination beam used to illuminate the object has insufficient uniformity, there are various techniques that may be used to precompensate the exposure of the hologram to achieve uniform reconstruction illumination. One such method includes using a mask with varying transmission which may be photographically or vacuum coated or otherwise produced which is placed before exposure of the hologram in the object beam and/or the reference beam to precompensate the exposure densities and thus fringe contrast in the recorded hologram to take into account the unevenness of the reconstruction illumination and thus yield a reconstructed diffraction illumination light field emitted from the hologram which is uniform in intensity and will thus uniformly illuminate the object under test.

During development of the holographic light diffractive grating, the exposed film structure may be left on the glass substrate and then processed with ultraviolet light and an optional heat cure, as prescribed by DuPont. However, for convenience, the exposed film structure was peeled off the glass substrate and relaminated to an acrylic substrate having a ⅛ inch thickness and an index of refraction of approximately 1.491. Thereafter, the exposed film structure can be UV cured in order to permanently fix the interference fringes within the film structure. Notably, the reason why the acrylic substrate is preferred during playback, is that it is more cost effective and, unlike glass, is not prone to breakage. Since the close index matching noted above is most important during recording of the hologram, the index differential of the acrylic substrate merely serves to shift the angle of incidence somewhat of the illuminating beam. However, as can be shown using graphs of the type depicted the acrylic substrate does not transmit the reconstructed light as efficiently as a closely matched substrate otherwise would.

One may alternatively use an intermediate index matching medium (e.g., fluid, glue or other adhesive) disposed between the light transmitting substrate and the holographic recording medium. In such instances, the index of refraction of the intermediate coupling medium should preferably be equal to the index of refraction of the light transmitting substrate 2, or the slanted grating optical element 3, or have an index of refraction between the index of refraction of the substrate 2 and the slanted grating optical element 3.

FIG. 12 shows an additional way of making the above referred to holograms. This general technique of making "total internal reflection holograms" is described, for example, by Stetson in Optik, Volume 29, at pages 520–537 (1969). The method shown in FIG. 12 is modified and improved over that described by Stetson because substrate 82 closely matches the index of refraction of the holographic medium 83 as noted above. In this optical recording arrangement, laser light is split into an object beam and a reference beam as is commonly done in the holographic art. Reference beam 80 impinges on prism 81 which is coupled to substrate 82 by way of an index matching fluid 85, whose index of refraction is desirably equal to the index of refraction of the substrate 82, or the prism 81, or somewhere in between those indices. A light absorber 86 is attached to the prism 81, as shown. Photosensitive holographic medium 83 is laminated or otherwise index matched or attached to substrate 82. Substrate 82 closely matches the refractive index of holographic medium 83 as noted above, and if any index matching or other attaching means is used between the substrate 82 and the holographic recording medium 83, its index of refraction must equal that of substrate 82 or holographic medium 83 or be somewhere in between those values. Object beam 84 strikes the holographic medium approximately perpendicular to it. The interference of the object beam and the reference beam cause slanted fringes to be formed within the holographic medium. The medium is then disattached from the prism and processed using known holographic recording medium processing techniques. The processed hologram is then laminated or otherwise attached to the light transmitting substrate 2 of the fingerprint imaging device of the present invention.

Oftentimes, it will be desirable to shape the wavefront of the (reconstruction) illumination beam with optics to match the wavefront used for the recording (reference) beam. This will minimize aberrations in the emitted first order beam, which is the conjugate of the original object beam. In some applications requiring extreme precision of measurement, minimizing these aberrations may be an important consideration. For applications with looser object illumination requirements, illumination with a more convenient wavefront, such as a spherical wavefront emanating from a small filament white light lamp, may produce perfectly satisfactory results.

Figure 13:
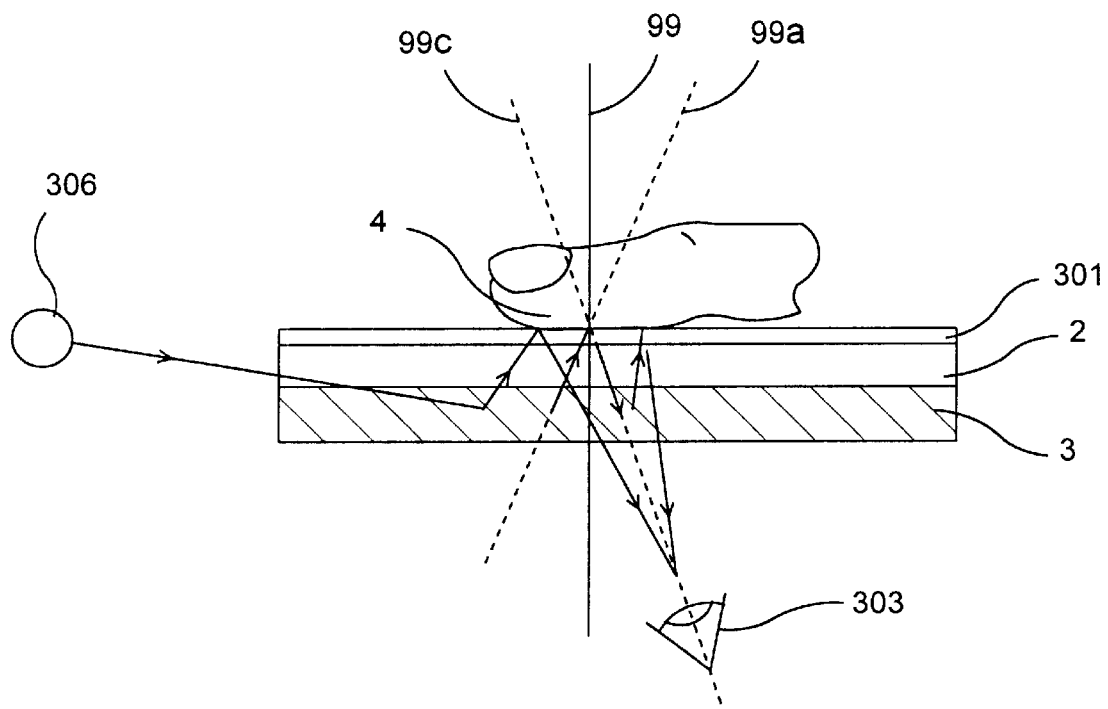
FIG. 13 is schematic diagram of the topographical image detector of the eighth illustrative embodiment of the present invention, in which the light transmitting substrate is arranged to support an object such as a finger, and to which is affixed a volume hologram embodying a slanted-fringe light diffractive grating designed to converge illuminating light rays reflected from the object towards a viewing system, such as the human eye.

In the topographic image detectors described above, the object (e.g., a finger) is illuminated using substantially collimated light rays produced from the slanted-fringe light diffractive gratings embodied in either the reflection or transmission volume holograms employed therein. Consequently, the size of the image detector 7b needs to be the same size as the illuminated object area to be viewed. In FIGS. 13, there is shown an eighth illustrative embodiment which is particularly useful when desiring to view an illuminated object, such as finger, using ones eyes. As shown in FIG. 13, the topographical image detector includes a reflection type hologram 3 mounted to light transmitting substrate 2 with a finger supporting region. The hologram embodies a light diffractive grating which causes modulated light from the illuminated object, to converge to a perspective point (e.g., the pupil of the viewer's eye) so that he or she may easily view the image therefrom, as shown. This configuration may also be used to detect images on a smaller image detector placed at the focal point of the light diffractive grating.

Figure 14:
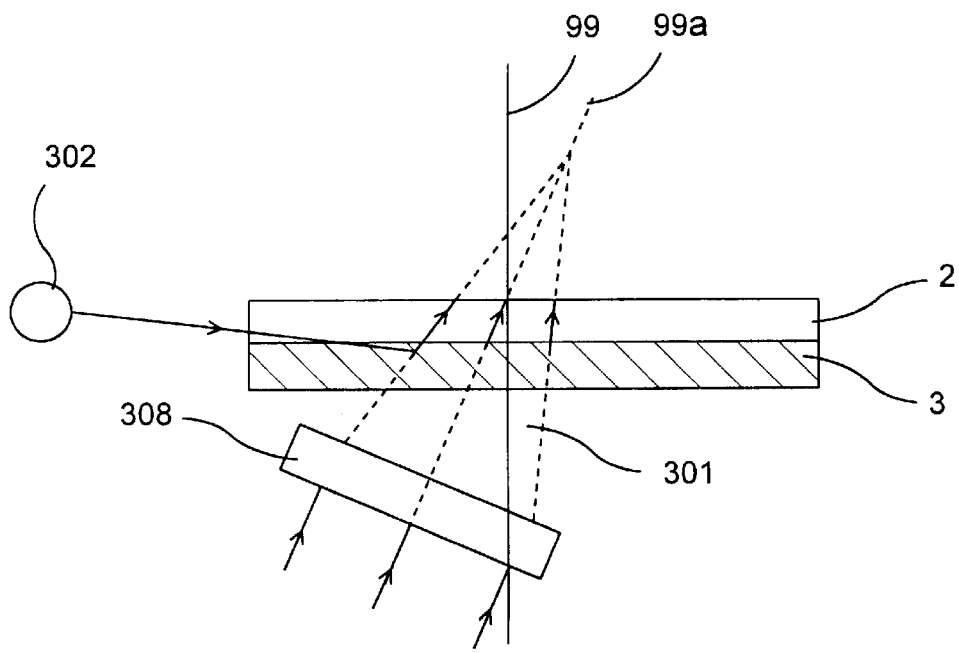
FIG. 14 is an optical arrangement for recording the slanted-fringe light diffractive grating in the volume hologram used in the eighth embodiment of the topographical image detector of the present invention shown in FIG. 11.

In FIG. 14, an optical recording arrangement is shown for making the reflection hologram used in the device of FIG. 13. In all other respects, the general method hereof can be followed to produce this type of light diffractive grating. As shown in FIG. 14, an object beam 300 is passed through a large low f-number lens 308, to illuminate holographic recording medium 3 with a converging light beam 301 which passes through the recording medium 3 and substrate 3 and converges to a point several inches below the substrate. The portion of the beam 301 within the recording medium 3 must be larger in diameter than the object desired to later be illuminated. The reference beam 302 enters the substrate 2 and interfering with the object beam 301 forms a slanted fringe grating within the recording medium. The object and reference beams are preferably s-polarized. Index matching of the substrate to the recording medium is carried out as described above. Similarly, the relamination and reillumination techniques described above may also be practiced.

During operation of the image detection device of FIG. 13, a reconstruction beam is transmitted through substrate 2 which causes a converging beam to be emitted from the hologram, illuminating the finger 4. A reflected converging light field, modulated by the topographic pattern of a fingerprint, is then reflected towards the image detector, in this case the viewer's eye 303. The entire illuminated fingerprint can be see by the naked eye of the viewer, or using a magnifying lens if desired for closer inspection.

In the eighth illustrative embodiment shown in FIG. 13, the reconstruction of the hologram produces what is known as the virtual image. Another possibility shown in FIG. 15 is to reconstruct the hologram with the conjugate of the original reference beam, which strikes the hologram from the opposite, 180 degrees from the original reference beam direction. In FIG. 15, a ninth illustrative embodiment of the image detector of the present invention is shown. This embodiment uses phase conjugate reconstruction during its operation. As shown in optical recording arrangement of FIG. 15A, the object beam 330, shown as a collimated light beam, strikes the recording medium 3 such that the reconstructed first order diffracted light beam will travel along optical axis 99c and have an angle with respect to optical axis 99a, which is less than the critical angle for the substrate and/or recording medium. Reference beam 331 enters and travels through light transmitting substrate 2 at an oblique angle, and then enters recording medium 3 in order to interfere with object beam 330, causing the formation of a slanted fringe grating within the recording medium. The criteria for index matching the substrate to the recording medium, substrate material selection, the use of s-polarized light and other recording features described hereinabove apply to the making of the ninth illustrative embodiment shown in FIG. 15A. After the hologram is processed, a replay superstrate 332 having characteristics matching those of other replay substrates described herein, is laminated, indexed matched or otherwise affixed to the opposite side of the recording medium, as shown in FIG. 15. It should be noted that alternatively, the superstrate may be affixed to the holographic recording medium prior to exposure of the hologram. As noted previously a narrow band pass filter 333 may be affixed or located proximate to the underside of hologram 3 or substrate 2, as shown. An image detector 334 is then located proximate to, or affixed to the underside surface of the narrow band pass filter 333 to complete the construction of the image detection device of the ninth illustrative embodiment. Optionally, substrate 2 can be eliminated from the device in order to achieve a thinner resulting geometry, as this optical element is not required for the phase conjugate replay geometry of this illustrative embodiment.

During operation of the image detection device of FIG. 15, reconstruction illumination light 336 travels through replay superstrate 332 in the direction approximately 180 degrees opposite the direction of the original reference beam. This causes the hologram to reconstruct the object beam, which illuminates finger 4. The modulated reflected light from the finger 4 then travels through the substrate 2 to the image detector 334 as has been described for previous embodiments.

In FIG. 16, a tenth illustrative embodiment of the image detection device of the present invention is illustrated. As shown, this embodiment comprises: an index discontinuity layer 320 disposed between a finger supporting layer 321 and reflection-type volume hologram 3; light transmitting substrate 2 affixed to hologram 3 with proper index matching requirements satisfied; an optional narrow band-pass filter 333 proximate to or affixed to the underside surface of substrate 2; and an image detection panel 334 proximate to, or affixed to narrow band-pass filter 333, (or substrate 2) as shown. The source of illumination 335 is arranged to enter through light transmitting substrate 2, from the opposite edge (i.e., transmission direction), so as not to satisfy the Bragg condition. The index discontinuity layer 320 should have an index of refraction low enough to cause total internal reflection of the illumination beam at the interface between layer 320 and light diffractive substrate 3. Layer 320, if not air, should also cause a reasonable index match to the protective layer 322 in order to avoid the formation of unwanted Moire fringes.

During operation, the illuminating beam passes from source 335 into substrate 2 and through reflection-type volume hologram 3, where it is reflected at the interface between hologram 3 and index discontinuity layer 320 (e.g., realized as an air gap or partial index matching medium). As shown in FIG. 16, the illumination beam is then reflected back into volume hologram 3 at the correct angle as the phase conjugate of the original reference beam, thus satisfying the Bragg condition. This causes the hologram to transmit a beam at the appropriate angle (e.g., slightly off perpendicular to the plane of the hologram) which then passes through index discontinuity layer 320, and protective cover layer 321, to illuminate finger 4 supported thereon. Reflected light modulated by the illuminated finger pattern is then reflected back through optical elements 320, 3, 2, and 333 onto image detection panel 334 as has been described for previous embodiments.

In FIG. 17, the image detection system of the present invention described hereinabove is shown realized in the form of a hand-supportable instrument 400 having a hand-supportable housing 401 having a head portion 401A and a handle portion 401B. Within the head portion, any of the image detection devices of the present invention 402 shown in the drawings hereof and described hereinabove, preferably incorporating an electronic (i.e., CCD) image detection array and associated electronics and buffer circuity, can be incorporated into this instrument. As shown, the head portion of this instrument has an image sensing window 403 through which the image detection region of the above-described image detection device can be mounted to enable the object (e.g., skin tissue) to be brought in physical contact therewith, as described hereinabove. In this embodiment of the present invention, the computer-based analyzer 206, 208 and the database and analysis subsystem 207 are realized within a computer workstation 404 having a central processor, keyboard, visual display, mouse-type pointing device and the like, with operating system and application software to carry out the functions of these subsystems. The images captured by the instrument of FIG. 17 are represented by digital data files that can be buffered in VRAM within housing portion 401B, and subsequently transmitted as output from the hand-supportable instrument 400, to computer workstation 404 over a flexible data transmission cable 405 using communication protocols well known in the art. In the illustrative embodiment, externally-mounted (e.g., button) 406 and internally-mounted control circuitry 407 are provided in order to initiate image scanning and capture by the instrument upon depressing the button 406. Once an image of an object is captured through sensing window 403 by the instrument, the digital image data can be processed, stored, analyzed, displayed and optionally printed out in the form of a hard-copy print. The instrument can be used in a doctor's office for in vivo dermatological examinations, including skin caner detection and other skin abnormalities. Each captured image can be recorded by data, with the patient's identification placed thereon and stored in an image database for future analysis.

In FIGS. 18A and 18B, another embodiment of the hand-supportable image detection instrument 410 is shown. As illustrated in FIG. 18A, the instrument has a hand-supportable housing 411 having a head portion 411A and a handle portion 411B. Within the head portion, any of the image detection devices of the present invention 412 shown in the drawings hereof and described hereinabove, preferably incorporating an electronic (CCD) image detection array and associated electronics and buffer circuitry, can be incorporated in this instrument. As shown, the head portion of this instrument has an image sensing window 413 through which the image detection region of the above-described image detection device can be mounted to enable the object (e.g., skin tissue) to be brought in physical contact therewith, as described hereinabove. Also, an LCD-based image viewing panel 414 is mounted within the rear section of the head portion of the housing. The function of the LCD image viewing panel 414 is to display the images of objects sensed (i.e. detected) through the image sensing window 413. In the illustrative embodiment, the LCD image viewing panel 414 and the image sensing window 413 are aligned substantially along the same axis, at about 90 or so degrees with respect to the longitudinal axis of the handle portion of the housing, providing as point and view capability to the instrument. In this embodiment of the present invention, images captured and displayed by the instrument of FIGS. 18A and 18B are also represented by digital data files that are buffered in VRAM within the housing, and subsequently transmitted as output from the hand-supportable instrument 410, to computer workstation 404 over a cordless RF-based digital data communication interface based on communication protocols well known in the art. This interface can be realized by installing an RF transceiver board 417A in the handle portion of instrument 410 and a matching RF transceiver board 417B within the base/stand unit 420 whose data communication port is in communication with the data communication port of computer workstation 404. Hand-supportable instrument 410 also incorporates a rechargeable battery supply 421 within its handle portion that automatically recharges when placed within its base/stand unit 420. In the illustrative embodiment, external trigger (e.g., button) 415 is provide on the handle portion of the housing in order to initiate image capture by the instrument upon depressing the button. Once an image is captured by the instrument, the image data can be locally processed stored in VRAM, and displayed on the LCD image viewing panel 414. This image data can be optionally transmitted to workstation 405 for processing, storage and subsequent analysis. The hand-held cordless instrument of FIGS. 18A and 18B can be used in a doctor's office for in vivo dermatological examinations, including skin caner detection and other skin abnormalities. Each captured image can be recorded by data, with the patient's identification placed thereon and stored in an image database for future analysis.

Having described the illustrative embodiments of the present, several modifications readily come to mind.

The slanted-fringe light diffractive grating may be recorded within the volume hologram of the image detection device so that light emitted from a LED or laser diode may be used for reconstruction (i.e., illumination).

The slanted fringe light diffraction gratings used in the device of the present invention may be embodied in non-holographic structures, using non-holographic recording techniques. An alternative holographic technique may include making slanted fringe gratings by immersing the recording medium in a large tank filled with an index matching fluid. In this approach to fringe grating production, the index matching fluid replace the substrate 2, but is subject to the same index matching versus input angle requirements illustrated in FIG. 13 and described hereinabove.

While a number of different embodiments have been described above, it is understood that the elements of such embodiments may be combined in accordance with the principles of the present invention to provide yet additional embodiments of the present invention. It is understood that while further modifications of the present invention will occur to persons with ordinary skill in the art, all such modifications are deemed to be within the scope and spirit of the present invention defined by the appended claims to the present invention.

What is claimed is:

1. A device for producing an image of a topographic surface having ridges and valleys, said device comprising:
   light producing means for producing light rays;
   a light transmitting substrate capable of transmitting the light produced by said light producing means;
   a topographic surface illuminating region for physical placement of an object having a topographical surface;
   an image detection means for detecting an image of said topographical surface;
   an optical element affixed to a portion of said light transmitting substrate and being disposed between said topographical surface illuminating region and said image detection means, said optical element embodying a light diffracting grating;
   wherein said topographic surface illuminating region and said optical element are each disposed substantially along a common optical axis; and
   wherein during the operation of said device,
   (1) light rays produced by said light producing means, propagate within said light transmitting substrate towards and into said optical element and are diffracted by said light diffracting grating,
   (2) diffracted light rays produced by said light diffracting grating, propagate directly towards said topographical surface illuminating region and fall incident upon and are intensity modulated by the ridges and valleys of said topographical surface, and
   (3) at least a portion of the intensity modulated light rays produced from said ridges and valleys of said topographical surface propagate back at an angle less than the critical angle of said light transmitting substrate through said light transmitting substrate and said optical element and fall incident upon said image detection means, whereupon an image of said topographical surface is detected.

2. The device of claim 1, wherein said light transmitting substrate has an upper surface in which said topographical surface illuminating region is disposed, and a lower surface arranged opposite said upper surface.

3. The device of claim 2, wherein said light diffracting grating comprises light diffracting structures that are slanted with respect to the upper and lower surfaces of said light transmitting substrate.

4. The device of claim 3, wherein said optical element is affixed to the lower surface of said light transmitting substrate.

5. The device of claim 4, wherein said light diffracting grating is a hologram containing a slanted fringe structure.

6. The device of claim 5, wherein said hologram is a volume hologram.

7. The device of claim 6, wherein said volume hologram is of the reflection type.

8. The device of claim 7, in which the index of refraction of said hologram closely matches that of said light transmitting substrate.

9. The device of claim 3, wherein said light transmitting substrate, said optical element and said light producing means are contained within a compact housing having an access aperture through which said topographical surface can be brought into physical contact with said light transmitting substrate, within said topographical surface illuminating region.

10. The device of claim 1, wherein said optical element is affixed to the upper surface of said light transmitting substrate, between said topographical surface illuminating region and said light transmitting substrate.

11. The device of claim 10, wherein said light diffracting grating is a hologram containing a slanted fringe structure.

12. The device of claim 11, wherein said hologram is a volume hologram.

13. The device of claim 12, wherein said volume hologram is of the transmission type.

14. The device of claim 10, which further comprises a light transmitting superstrate affixed to said upper surface of said optical element, and in which said topographical surface illuminating region is disposed.

15. The device of claim 14, wherein said light transmitting substrate, said optical element, said superstrate and said light producing means are contained within a compact housing having an access aperture through which said topographical surface can be placed in physical contact with said light transmitting superstrate, within said topographical surface illuminating region.

16. The device of claim 1, wherein said image detection means is an electro-optical image detector.

17. The device of claim 16, wherein said electro-optical image detector is an image detection array.

18. The device of claim 1, wherein said light producing source produces substantially monochromatic light.

19. The device of claim 1, wherein said light producing source comprises a white light source for producing white light.

20. The device of claim 19, which further comprises a narrow wavelength bandpass filter disposed between said white light source and said light transmitting substrate.

21. The device of claim 1, which further comprises a narrow wavelength bandpass filter disposed substantially along said optical axis and between said optical element and said image detection means.

22. The device of claim 1, which further comprises an image transfer means disposed between said image detection means and said optical element.

23. The device of claim 22, wherein said image transfer means is a structure selected from the group consisting of a lens system, a microchannel plate, a fiber optic array, and a micro-lens array.

24. The device of claim 1, in combination with an image storage means for storing images produced by said image detection means.

25. The combination of claim 24, which further comprises an image analyzer and an image database.

26. The device of claim 1, which further includes electronic circuitry for interfacing said image detection means with a computer-based system.

27. The device of claim 1, wherein said light producing means is a structure selected from the group consisting of a monochromatic light source, a small filament incandescent lamp, and a light emitting diode.

28. The device of claim 1, wherein said light diffracting grating produces converging light rays when said light rays strike said light diffracting grating.

29. The device of claim 1, wherein said light diffracting grating produces substantially collimated light rays when said light beam strikes said light diffracting grating.

30. The device of claim 1, wherein said light diffracting grating produces diverging light rays when said light rays strike said light diffracting grating.

31. The device of claim 1, wherein the indices of refraction of said light transmitting substrate and said optical element are matched to optimize light transmission efficiency therebetween.

32. The device of claim 1, wherein light rays produced from said light producing means strike said light diffracting-grating such that the first diffraction order of said diffracted light travels at an angle with respect to said optical axis, which is less than the critical angle for said light transmitting substrate and/or said optical element.

33. The device of claim 1, wherein said topographical surface illuminating region is associated with a portion of said light transmitting substrate about said optical axis.

34. The device of claim 1, wherein said topographical surface illuminating region is associated with a portion of said optical element about said optical axis.

35. The device of claim 1, which further comprises a light transmitting substrate operably associated with said optical element.

36. The device of claim 1, which further comprises a PCMCIA-type housing containing said light producing means, said light transmitting substrate, said optical element, and said image detection means.

37. The device of claim 1, wherein said topographical surface illuminating region, said optical element and said image detection means are each disposed substantially along said common optical axis.

38. The device of claim 37, wherein said detected image includes information corresponding to said ridges and valleys of said topographical surface.

39. The device of claim 38, wherein said topographical surface is a fingerprint.

40. The device of claim 36, wherein said topographical surface is a sample of skin tissue.

41. The device of claim 1, wherein said diffracted light rays propagate toward said topographical surface illuminating region at an angle less than the critical angle of said light transmitting substrate.

42. The device of claim 41, wherein said portion of the intensity modulated light rays propagate back through said light transmitting substrate and said optical element at an angle less than the critical angles of said light transmitting element and said optical element.

43. The device of claim 42, in which the light rays produced by said topographical surface travel along a second optical axis different from said common optical axis.

44. The device of claim 43, wherein said second optical axis is offset from the axis of the peak Bragg angle for said light diffracting grating.

45. The device of claim 43, in which the optical axis of said image detection means is along said second optical axis.

46. The device of claim 1, further comprising a second light diffracting grating secured to the upper surface of said light transmitting substrate and spaced thereon from said first mentioned light diffracting grating, said light producing means being positioned to transmit light through said light transmitting surface to said second light diffracting grating, wherein light diffracted from said second light diffracting grating propagates within said light transmitting substrate toward said first light diffracting grating at an angle greater than the critical angle for said light transmitting substrate.

47. The device of claim 46, in which the index of refraction of said second light diffracting grating closely matches that of said light transmitting substrate.

48. The device of claim 1, further comprising a second light diffracting grating secured to the underside of said light transmitting substrate and spaced thereon from said first mentioned light diffracting grating, said light producing means being positioned beneath and in optical communication with said second light diffracting grating, wherein light diffracted from said second light diffracting grating propagates within said light transmitting substrate at an angle greater than the critical angle of said light transmitting substrate to pass into and illuminate said first-mentioned light diffraction grating.

49. The device of claim 1, in which said light diffracting grating is operatively secured to the underside of said light transmitting surface, and said image detection means is operatively secured to the underside of said light diffracting grating.

50. The device of claim 49, further including a narrow bandpass optical filter interposed and operatively secured to said light diffracting grating and said image detection means.

51. The device of claim 1, in which said light diffracting grating is operatively secured to the upper surface of said light transmitting substrate, and said image detecting means is operatively secured to the underside of said light transmitting substrate.

52. The device of claim 1, further comprising first polarizing means adjacent the underside of said light diffracting grating, said image detection means being operatively secured to the underside of said first polarizing means.

53. The device of claim 52, further comprising second polarizing means optically interposed intermediate said light producing means and said light transmitting substrate.

54. The device of claim 53, in which said first polarizing means is a P- polarizing filter and said second polarizing means is an S-polarizing filter.

55. The device of claim 54, further comprising a phase-retardation plate operatively secured to the upper surface of said light transmitting substrate.

56. The device of claim 1, further comprising narrow band pass filter means interposed intermediate said light producing means and said light diffraction grating for matching the wavelength of the Bragg condition for said light diffracting grating.

57. The device of claim 1, wherein light rays returning from the object are diffracted by said light diffracting grating at an angle that meets the Bragg condition, are diffracted by said light diffracting grating at an angle less than the critical angle of said light transmitting substrate, and pass out of said light transmitting substrate to said image detection means.

58. A hand-supportable instrument for producing an image of a topographical surface, comprising:

a hand-supportable housing; and said device of claim 1 disposed within said hand-supportable housing.

59. The hand-supportable instrument of claim 58, wherein said hand-supportable housing comprises a head portion having an image sensing window, and a handle portion supportable within the hand of a user.

60. The hand-supportable instrument of claim 59, wherein said device is disposed within said head portion, and said topographical surface illuminating region of said device is aligned with said image sensing window to allow the topographical surface of said object to be imaged through said image sensing window.

61. The hand-supportable instrument of claim 60, which further comprise a cordless RF-based communication interface between said device and a base unit operably connectable to a host computer system.

62. The hand-supportable instrument of claim 61, which further comprise a rechargeable power supply disposed within said hand-supportable housing and a battery recharger disposed within said base unit, and wherein said base unit has a recess for receiving and supporting said hand-supportable housing so as to allow recharging of said rechargeable battery supply while supported therein.

63. A topographical image detector comprising a light source, an object supporting light transmitting layer, a volume hologram, an index discontinuation layer interposed between said object supporting layer and said hologram, a light transmitting substrate affixed to said hologram, and image detecting means in optical communication with said light transmitting substrate, wherein 1) light from said light source passes through said light transmitting substrate and said volume hologram and is then reflected at the interface of said hologram and said index discontinuity layer and is then reflected back into said volume hologram at an angle satisfying the Bragg condition;

2) said hologram diffracts the light which passes through said index discontinuity layer and said object supporting layer to illuminate the object supported therein, and 3) reflected light modulated by the surface pattern of the object is then reflected back through said index discontinuously layer, said hologram, and said light transmitting medium to said image detection means.

64. The device of claim 63, therein said index discontinuity layer comprises air or a partial index matching medium.

65. The device of claim 63, further comprising a bandpass filter optically interposed between said light transmitting substrate and said image detection means.

* * * * *